US009220468B2

(12) United States Patent
Kitamura et al.

(10) Patent No.: US 9,220,468 B2
(45) Date of Patent: Dec. 29, 2015

(54) ENDOSCOPE OBSERVATION ASSISTANCE SYSTEM, METHOD, APPARATUS AND PROGRAM

(75) Inventors: Yoshiro Kitamura, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 388 days.

(21) Appl. No.: 13/636,829

(22) PCT Filed: Mar. 30, 2011

(86) PCT No.: PCT/JP2011/001937
§ 371 (c)(1),
(2), (4) Date: Sep. 24, 2012

(87) PCT Pub. No.: WO2011/122037
PCT Pub. Date: Oct. 6, 2011

(65) Prior Publication Data
US 2013/0018255 A1 Jan. 17, 2013

(30) Foreign Application Priority Data
Mar. 31, 2010 (JP) .................................. 2010-083604

(51) Int. Cl.
*A61B 1/04* (2006.01)
*A61B 6/12* (2006.01)
*A61B 1/00* (2006.01)
(Continued)

(52) U.S. Cl.
CPC ............... *A61B 6/12* (2013.01); *A61B 1/00009* (2013.01); *A61B 19/5244* (2013.01); *G06T 19/003* (2013.01); *A61B 19/5212* (2013.01);
(Continued)

(58) Field of Classification Search
CPC ........... A61B 19/5212; A61B 19/5244; A61B 1/00009; A61B 2019/5255; A61B 6/12; G06T 19/003; G06T 2200/04; G06T 2210/41
USPC ................. 600/101, 103, 104, 111, 424, 476; 382/128
See application file for complete search history.

(56) References Cited

U.S. PATENT DOCUMENTS

| 2002/0128547 A1 | 9/2002 | Furuhashi et al. |
| 2005/0018888 A1 | 1/2005 | Zonneveld |

(Continued)

FOREIGN PATENT DOCUMENTS

| JP | 2002-119507 | 4/2002 |
| JP | 2002-263053 | 9/2002 |

(Continued)

OTHER PUBLICATIONS

Chinese Office Action dated Jul. 21, 2014 in corresponding Chinese Patent Application No. 201180016319.8 with English translation.

(Continued)

*Primary Examiner* — Michael Rozanski
(74) *Attorney, Agent, or Firm* — Young & Thompson

(57) ABSTRACT

A virtual endoscope image generation unit receives, as an input, a three-dimensional medical image formed by a three-dimensional medical image formation unit, and generates a virtual endoscope image representing the body cavity viewed from a position in the three-dimensional medical image corresponding to the position of a treatment tool detected in real time by a treatment tool position detection unit. The generated virtual endoscope image is displayed on a WS display.

21 Claims, 26 Drawing Sheets

(51) Int. Cl.
*G06T 19/00* (2011.01)
*A61B 19/00* (2006.01)

(52) U.S. Cl.
CPC ..... *A61B2019/5255* (2013.01); *G06T 2200/04* (2013.01); *G06T 2210/41* (2013.01)

(56) References Cited

U.S. PATENT DOCUMENTS

| | | | |
|---|---|---|---|
| 2008/0207997 A1* | 8/2008 | Higgins et al. | 600/114 |
| 2008/0247619 A1 | 10/2008 | Li | |
| 2011/0245660 A1* | 10/2011 | Miyamoto | 600/424 |
| 2012/0327186 A1* | 12/2012 | Kitamura et al. | 348/45 |
| 2013/0023730 A1* | 1/2013 | Kitamura et al. | 600/104 |

FOREIGN PATENT DOCUMENTS

| | | |
|---|---|---|
| JP | 2004-097696 | 4/2004 |
| JP | 2005-021353 | 1/2005 |
| JP | 2005-511234 | 4/2005 |
| JP | 2007-029232 | 2/2007 |
| JP | 2008-245719 | 10/2008 |
| WO | WO 2010/024331 | 3/2010 |

OTHER PUBLICATIONS

International Search Report, PCT/JP2011/001937, Jul. 12, 2011.
Official Action from Japanese Patent Office issued Aug. 27, 2013; Patent Application No. 2010-083604 with partial english translation.

* cited by examiner

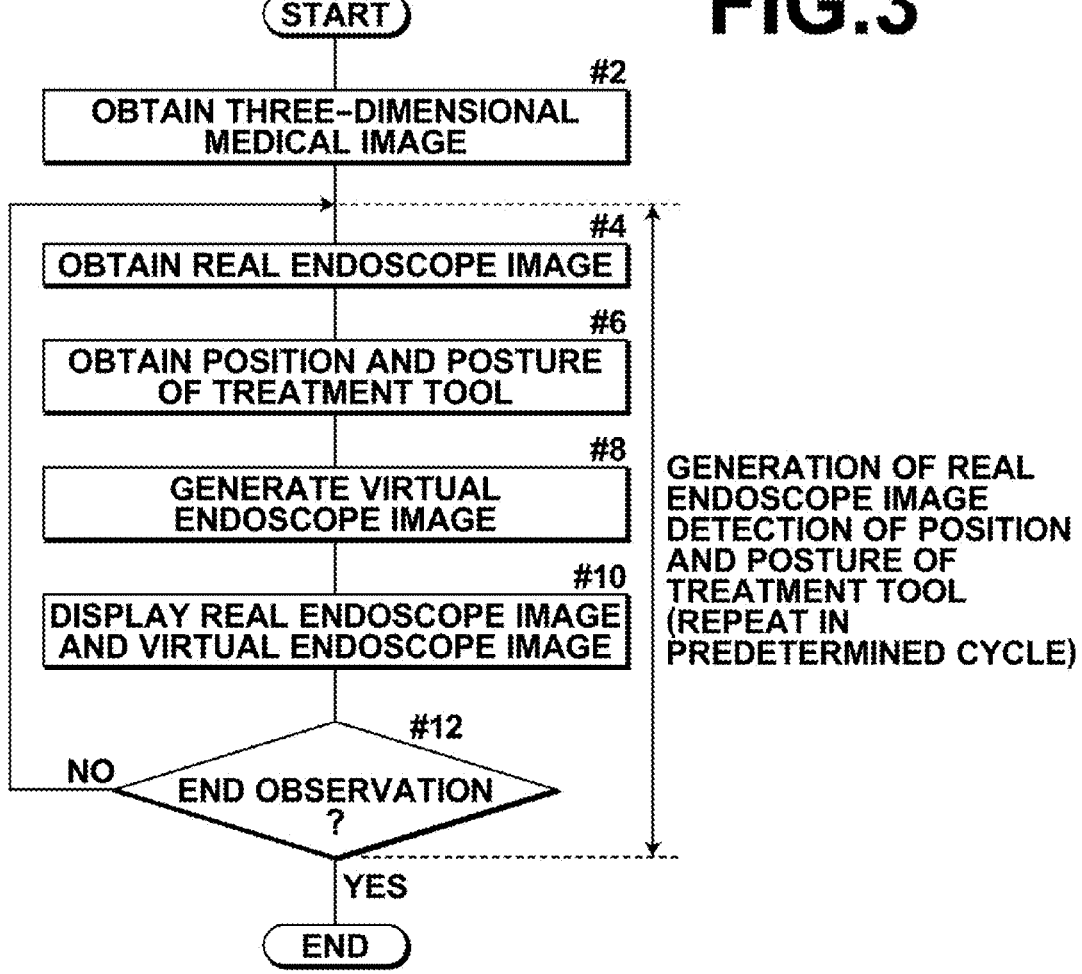

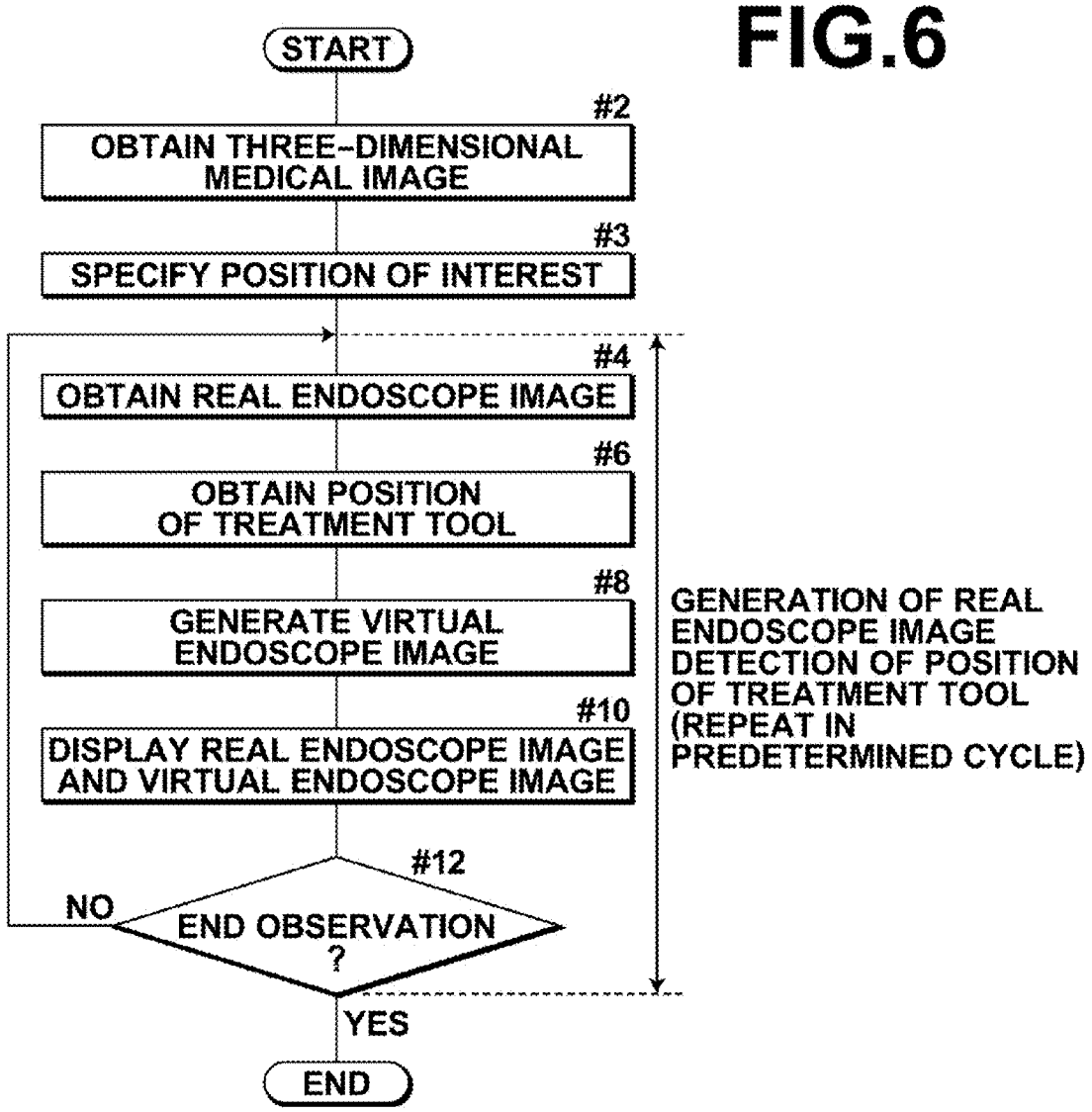

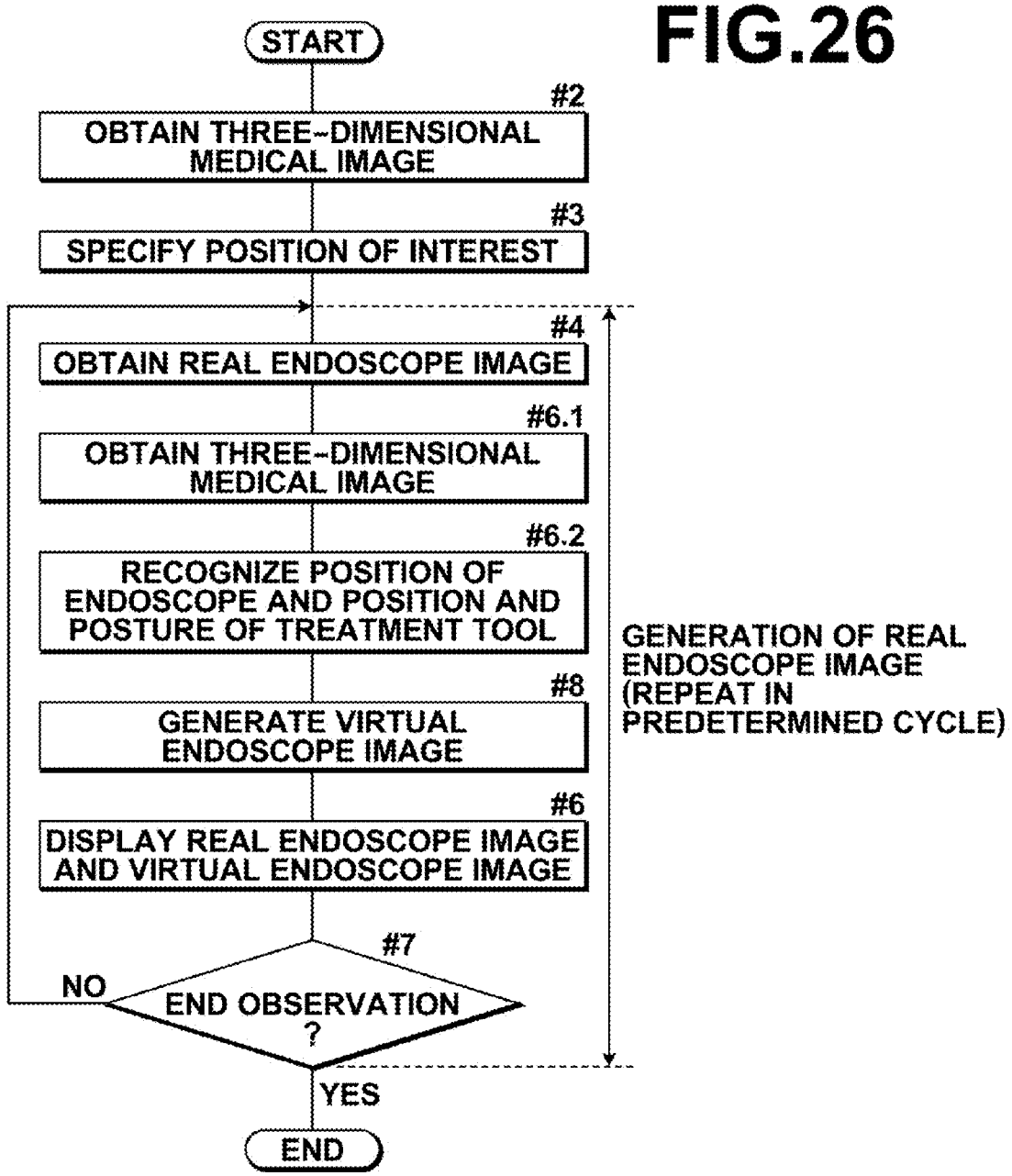

ENDOSCOPE OBSERVATION ASSISTANCE SYSTEM, METHOD, APPARATUS AND PROGRAM

BACKGROUND OF THE INVENTION

1. Field of the Invention

The present invention relates to a technique for assisting endoscopic observation in an endoscopic surgery, an endoscopic examination and the like with an endoscope inserted into the body cavity of a subject to be examined. Especially, the present invention relates to a technique for assisting endoscopic observation by using a virtual endoscope image representing the body cavity of the subject to be examined.

2. Description of the Related Art

In recent years, endoscopic surgeries, such as a laparoscopic surgery and a thoracoscopic surgery, drew attention. The endoscopic surgeries do not require laparotomy, thoracotomy, and the like. The endoscopic surgeries require incision only to form two or three holes with diameters of approximately a few centimeters for introduction of an endoscope and a treatment tool. Therefore, the endoscopic surgeries have a merit that a burden on a patient is extremely low. However, a surgery in a narrow field of view of the endoscope is technically difficult, and an operation needs to be performed by a skilled doctor. If a blood vessel or an organ of a patient is damaged by mistake, and bleeding occurs, the endoscopic surgery must be switched to a conventional surgery including laparotomy, thoracotomy, or the like.

Meanwhile, a virtual endoscope technique for generating an image similar to an endoscopic image from three-dimensional volume data obtained by imaging by CT or the like is known. This technique is widely used in North America especially to detect a tumor in a large intestine only by imaging by CT without performing an endoscopic examination.

Further, a technique for assisting an endoscopic surgery by using a virtual endoscope image has been proposed.

For example, Japanese Unexamined Patent Publication No. 2002-263053 (Patent Document 1) discloses an apparatus for displaying a real endoscope image obtained by imaging by an endoscope and a virtual endoscope image in such a manner to be superimposed one on the other. In Patent Document 1, the position of the endoscope is detected by a sensor, and the detected position is used as a viewpoint to generate the virtual endoscope image having an angle of view wider than that of the endoscope.

Further, Japanese Unexamined Patent Publication No. 2005-021353 (Patent Document 2) discloses an apparatus for displaying a synthesis image and a real endoscope image. In Patent Document 2, the position of an endoscope is detected in real time, and a virtual endoscope image having the same field of view as that of the endoscope, and that visualizes an arrangement of blood vessels in the field of view is generated. Further, the position of a treatment tool used in an endoscopic surgery is detected in real time, and the synthesis image representing the treatment tool at the position of the treatment tool in the virtual endoscope image is generated.

In the techniques disclosed in these documents, a narrow field of view of an endoscope may be supplemented with a virtual endoscope image. However, the viewpoint of the virtual endoscope image is the same as that of a real endoscope image, and an observation direction of the virtual endoscope image is the same as that of the real endoscope image. Therefore, a region of interest, such as a region on which a surgery is to be performed, and a treatment tool may not be displayed in the virtual endoscope image and the real endoscope image, depending on a positional relationship among the region of interest, the treatment tool and the endoscope, and such a positional relationship may not be recognized.

Further, it is difficult to perspectively recognize an endoscope image. Therefore, in the virtual endoscope image and the real endoscope image displayed by using the techniques disclosed in these documents, it may be difficult to recognize a state in which a treatment tool becomes close to a region of interest.

SUMMARY OF THE INVENTION

In view of the foregoing circumstances, it is an object of the present invention to provide a system, a method, an apparatus and a program that can make it possible to more definitely recognize a positional relationship between a region of interest, such as a region on which a surgery is to be performed, and a treatment tool, and a state in which the treatment tool becomes close to the region of interest during endoscopic observation of the body cavity of a subject to be examined by an endoscope inserted into the body cavity.

An endoscope observation assistance system of the present invention comprises:

a three-dimensional medical image formation means that forms a three-dimensional medical image representing the body cavity of a subject to be examined;

a treatment tool position detection means that detects, in real time, the position of a treatment tool inserted into the body cavity;

a virtual endoscope image generation means that receives the three-dimensional medical image as an input, and generates a virtual endoscope image representing the body cavity viewed from a corresponding treatment tool position, which is a position in the three-dimensional medical image corresponding to the detected position of the treatment tool; and a display means that displays the virtual endoscope image.

An endoscope observation assistance method of the present invention comprises the steps of:

forming a three-dimensional medical image representing the body cavity of a subject to be examined;

detecting, in real time, the position of a treatment tool inserted into the body cavity;

receiving the three-dimensional medical image as an input, and generating a virtual endoscope image representing the body cavity viewed from a corresponding treatment tool position, which is a position in the three-dimensional medical image corresponding to the detected position of the treatment tool; and displaying the virtual endoscope image.

An endoscope observation assistance apparatus of the present invention comprises:

a three-dimensional medical image obtainment means that obtains a three-dimensional medical image representing the body cavity of a subject to be examined;

a treatment tool position obtainment means that obtains the position of a treatment tool inserted into the body cavity, and the position having been detected in real time by a position detection means;

a virtual endoscope image generation means that receives the three-dimensional medical image as an input, and generates a virtual endoscope image representing the body cavity viewed from a corresponding treatment tool position, which is a position in the three-dimensional medical image corresponding to the obtained position of the treatment tool; and a display control means that makes a display means display the virtual endoscope image.

An endoscope observation assistance program of the present invention causes a computer to execute the steps of:

obtaining a three-dimensional medical image representing the body cavity of a subject to be examined;

obtaining the position of a treatment tool inserted into the body cavity, and the position having been detected in real time by a position detection means;

receiving the three-dimensional medical image as an input, and generating a virtual endoscope image representing the body cavity viewed from a corresponding treatment tool position, which is a position in the three-dimensional medical image corresponding to the obtained position of the treatment tool; and making a display means display the virtual endoscope image.

The present invention will be described in detail.

In the present invention, a direction in which a treatment tool moves straight forward may be detected at the same time as detection of the position of the treatment tool. Further, a virtual endoscope image in which image information on a visual line (treatment tool visual line) from a corresponding treatment tool position is projected may be generated, and the treatment tool visual line having a direction in the three-dimensional medical image corresponding to the detected direction in which the treatment tool moves straight forward. A specific example of such a virtual endoscope image is a virtual endoscope image in which a treatment tool visual line is a visual line (center visual line) at the center of the field of view of the virtual endoscope image. Further, the virtual endoscope image may identifiably represent a position in the virtual endoscope image at which the image information on the treatment tool visual line has been projected.

Further, in the present invention, the position of a (first) structure of interest in the body cavity in the three-dimensional medical image may be specified as a (first) position of interest. Further, a virtual endoscope image, the field of view of which includes the specified (first) position of interest, may be generated. A specific example of such a virtual endoscope image is a virtual endoscope image in which a visual line from the corresponding treatment tool position toward the specified (first) position of interest is a center visual line of the virtual endoscope image. Further, the virtual endoscope image may identifiably represent at least the (first) position of interest in the (first) structure of interest.

Here, specific examples of the "(first) structure of interest" are a region on which an endoscopic surgery is to be performed, an anatomical structure that requires caution in a surgery, and the like. Specifically, the "(first) structure of interest" is a blood vessel, an organ, a tumor or the like. A specific method for specifying the position of the (first) structure of interest may be an automatic method using a known image recognition technique, a method by a manual operation by a user, or these methods may be used in combination.

Further, in the present invention, a warning may be presented when a corresponding treatment tool position and a (first) structure of interest are close to each other to such a extent to satisfy a predetermined criterion. The warning may be visually presented in a virtual endoscope image or the like. Alternatively, the warning may be presented by using a method that appeals to another sense organ.

Further, in the present invention, a second structure of interest in the body cavity in the three-dimensional medical image may be detected. Further, a virtual endoscope image that identifiably represents the detected second structure of interest may be generated. Here, specific examples of the "second structure of interest" are similar to the examples of the first structure of interest. Therefore, for example, the first structure of interest may be a region on which an endoscopic surgery is to be performed, and the second structure of interest may be an anatomical structure that requires caution in a surgery, or vice versa.

In the present invention, the position of an endoscope inserted into the body cavity may be detected. Further, a virtual endoscope image, the field of view of which includes a position (corresponding endoscope position) in a three-dimensional medical image corresponding to the detected position of the endoscope, may be generated, and the virtual endoscope image may identifiably represent the corresponding endoscope position.

Here, when the three-dimensional medical image was obtained before endoscopic observation, an endoscope was not inserted into the body cavity of a subject to be examined during imaging or obtainment of the three-dimensional medical image. Therefore, when a virtual endoscope image is generated, a marker or the like representing an endoscope should be synthesized at a position in the virtual endoscope image corresponding to the position detected by a position detection means. In contrast, when a three-dimensional medical image is obtained in real time during endoscopic observation, and an endoscope is represented in the three-dimensional medical image, a virtual endoscope image should be generated in such a manner that the endoscope is rendered also in the virtual endoscope image.

Further, in the present invention, a real endoscope image representing the body cavity may be formed by imaging in real time by an endoscope. Further, a real endoscope image formed substantially at the same timing as detection of the position of the treatment tool used at the time of generation of the virtual endoscope image may be displayed together with the virtual endoscope image. Accordingly, the real endoscope image formed in real time by imaging by an endoscope and a virtual endoscope image viewed from the position of a treatment tool that has been detected in real time by a position detection means substantially at the same timing as formation of the real endoscope image are displayed.

Further, when generation of a virtual endoscope image is repeated based on detection of the position of a treatment tool, the real endoscope image and the virtual endoscope image are updated in real time based on the movement of the treatment tool.

Here, the real endoscope image and the virtual endoscope image may be displayed on a display device. Alternatively, the real endoscope image and the virtual endoscope image may be displayed separately on plural display devices. The plural display devices may be set, next to each other, at physically the same place so that the two images are observable at the same time. Alternatively, the plural display devices may be set physically away from each other so that the two images are observed separately.

Further, the expression "a virtual endoscope image, the field of view of which includes the (first) position of interest", and the expression "a virtual endoscope image, the field of view of which includes a corresponding endoscope position" mean that image information on a visual line from a viewpoint (corresponding treatment tool position) toward the (first) position of interest or toward the corresponding endoscope position should be reflected in the virtual endoscope image. For example, when a structure, such as an organ, a blood vessel, and a fold, is present between the treatment tool and the (first) structure of interest or the endoscope, it is not always necessary that the endoscope or the (first) structure of interest is represented in the virtual endoscope image.

When the "virtual endoscope image" is generated, a distance from the corresponding treatment tool position to a surface of a structure in the body cavity may be used as an element for determining pixel values of the virtual endoscope image. Further, a color template that is defined so that an external view of each part in the body cavity represented in the virtual endoscope image is substantially the same as an external view of each part in the body cavity represented in a real endoscope image may be used. Here, for example, the color template may define in such a manner that the color of each part in the body cavity in the virtual endoscope image is substantially the same as the color of each part in the body cavity in the real endoscope image. Further, the color template may be defined in such a manner that each part in the body cavity in the virtual endoscope image is represented semi-transparently, if necessary, so that a back-side structure, which is not observable by being blocked by an object or the like present on the front side of the back-side structure in a real endoscope image, is recognized.

In the present embodiment, when formation and obtainment of a three-dimensional medical image is performed during endoscopic observation, the three-dimensional medical image may be obtained in real time. In that case, the position of an endoscope or a treatment tool may be detected by performing image recognition processing on the three-dimensional medical image.

In the present invention, a three-dimensional medical image representing the body cavity of a subject to be examined is received as an input, and a virtual endoscope image representing the body cavity viewed from a corresponding position in the three-dimensional medical image, which corresponds to the position of the treatment tool inserted into the body cavity, is generated, and the position having been detected in real time. Further, the virtual endoscope image is displayed. Here, the displayed virtual endoscope image is generated as if the treatment tool is an endoscope. Therefore, it is possible to observe the body cavity from the viewpoint of the treatment tool. When the virtual endoscope image is used in combination with a real endoscope image, it is possible to observe the body cavity from various angles. Therefore, it becomes possible to more definitely recognize the positional relationship between the region of interest and the treatment tool. Further, it becomes possible to more definitely recognize a state in which a treatment becomes close to a region of interest. Hence, it is possible to prevent a mistake in a procedure or the like during a surgery, an examination or the like.

At this time, the viewpoint of the virtual endoscope is changed in real time based on feedback of a result of detecting the position of a treatment tool in real time, and virtual endoscope images from changed viewpoints are continuously displayed. Therefore, it is possible to dynamically and more appropriately recognize a state in which a treatment tool becomes close to a structure of interest.

Further, a real endoscope image representing the body cavity may be formed by imaging in real time by an endoscope, and the real endoscope image formed substantially at the same timing as detection of the position and the posture of the treatment tool used at the time of generation of a virtual endoscope image may be displayed together with the virtual endoscope image. In such a case, the displayed real endoscope image and virtual endoscope image represent the state of the body cavity substantially at the same point of time. Further, the real endoscope images and the virtual endoscope images are continuously displayed in such a manner that they are temporally synchronized with each other. At this time, if generation of a virtual endoscope image is repeated based on detection of the position of the treatment tool, the real endoscope image and the virtual endoscope image are updated in real time. Specifically, the field of view of the real endoscope image changes in such a manner to be linked with an operation, such as a movement and rotation of the endoscope. Further, it is possible to change the field of view of the virtual endoscope image in such a manner to be linked with an operation, such as the movement of the treatment tool. As described above, it is possible to observe the body cavity by using the real endoscope image and the virtual endoscope image in such a manner that they supplement each other.

BRIEF DESCRIPTION OF THE DRAWINGS

FIG. 3 is a flow chart illustrating a flow of endoscope observation assistance processing in the first embodiment of the present invention;

FIG. 6 is a flow chart illustrating a flow of endoscope observation assistance processing in the second embodiment of the present invention;

FIG. 26 is a flow chart illustrating a flow of endoscope observation assistance processing in the eleventh embodiment of the present invention.

DESCRIPTION OF THE PREFERRED EMBODIMENTS

Hereinafter, an endoscope observation assistance system according to embodiments of the present invention will be described.

Figure 1:
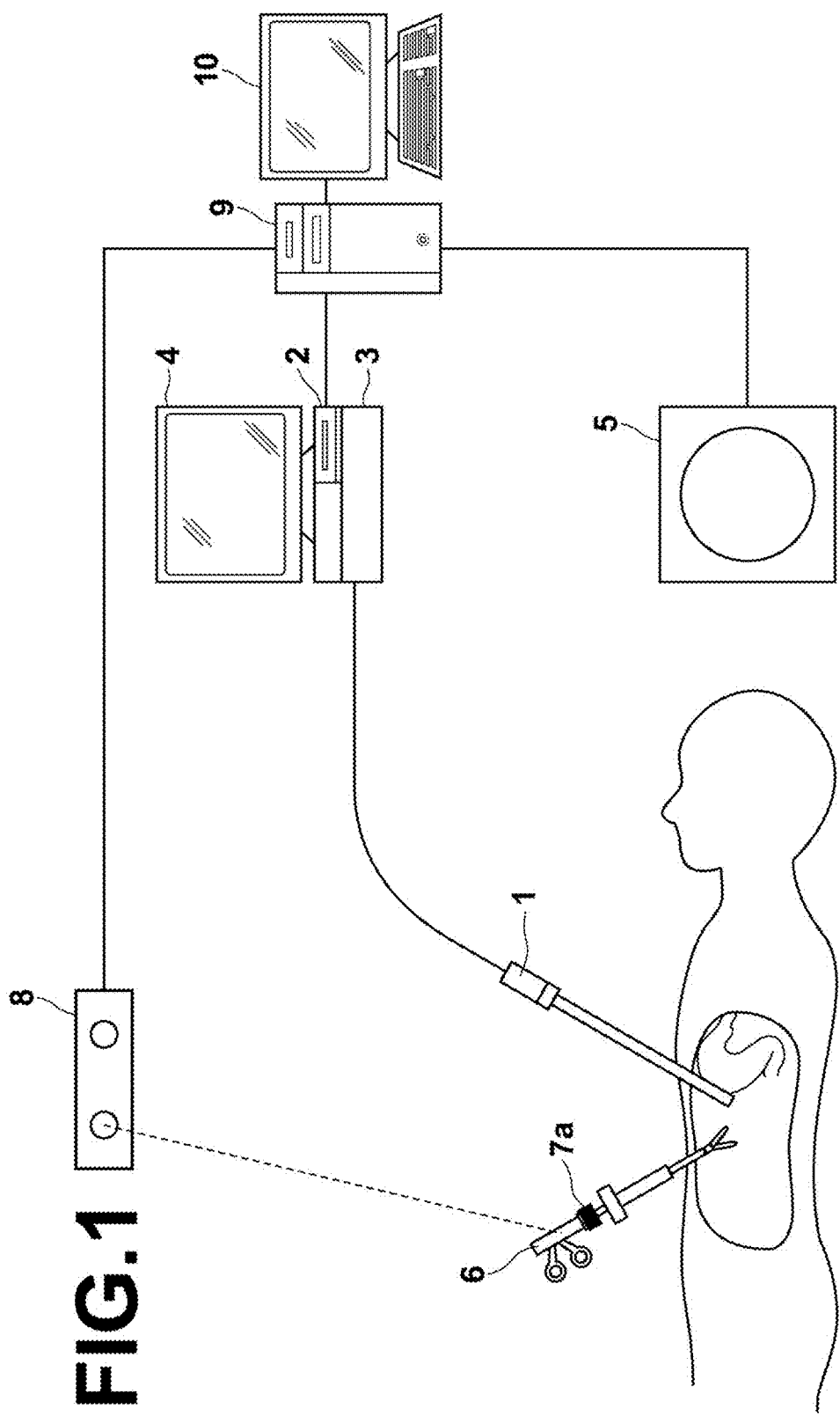
FIG. 1 is a schematic diagram illustrating the hardware configuration of an endoscope observation assistance system according to first through ninth embodiments of the present invention.

FIG. 1 is a schematic diagram illustrating the hardware configuration of an endoscope observation assistance system according to a first embodiment of the present invention. As illustrated in FIG. 1, this system includes an endoscope 1, a digital processor 2, a light source apparatus 3, a display 4 for a real endoscope image, a modality 5, a treatment tool 6, a marker 7a for the treatment tool, a position sensor 8, an image processing workstation 9, and a display 10 for an image processing workstation (hereinafter, WS display).

In the present embodiment, the endoscope 1 is a rigid endoscope for an abdominal cavity, and the endoscope 1 is inserted into the abdominal cavity of a subject to be examined. Light guided from the light source apparatus 3 by an optical fiber is output from a leading end of the endoscope 1, and an image of the inside of the abdominal cavity of the subject to be examined is obtained by an imaging optical system of the endoscope 1. The digital processor 2 transforms imaging signals obtained by the endoscope 1 into digital image signals. After the digital processor 2 corrects an image quality by performing digital signal processing, such as white balance adjustment and shading correction, the digital processor 2 attaches supplementary information defined by DICOM (Digital Imaging and Communications in Medicine) standard, and outputs real endoscope image data ($I_{RE}$). The output real endoscope image data ($I_{RE}$) are sent to the image processing workstation 9 through LAN in accordance with a communication protocol based on DICOM standard. Further, the digital processor 2 transforms the real endoscope image data ($I_{RE}$) to analog signals, and outputs the analog signals to the display 4 for a real endoscope image. Accordingly, the display 4 for a real endoscope image displays the real endoscope image ($I_{RE}$). Since obtainment of imaging signals by the endoscope 1 is performed at a predetermined frame rate, the display 4 for a real endoscope image displays the real endoscope image ($I_{RE}$), as a dynamic image representing the inside of the abdominal cavity. Further, the endoscope 1 may also perform still image imaging based on an operation by a user.

The modality 5 is an apparatus for generating image data (V) of a three-dimensional medical image representing a region to be examined of a subject to be examined by imaging the region to be examined. Here, the modality 5 is a CT apparatus. Supplementary information defined by DICOM standard has been attached also to the three-dimensional medical image data (V). Further, the three-dimensional medical image data (V) are also sent to the image processing workstation 9 through LAN in accordance with a communication protocol based on DICOM standard.

The marker 7a for a treatment tool and the position sensor 8 constitute a known three-dimensional position measurement apparatus. The marker 7a for a treatment tool is provided in the vicinity of a handle part of the treatment tool 6, and the optical position sensor 8 detects the three-dimensional position of the marker 7a with predetermined time intervals. The marker 7a for a treatment tool is composed of plural pieces of marker. Therefore, the position sensor 8 can detect also the posture of the treatment tool 6 based on the positional relationship among the pieces of marker. Here, the posture of the treatment tool 6 is a vector representing a direction in which the treatment tool is inserted, and the posture is the same as a direction in which the treatment tool moves straight forward. Further, it is possible to calculate three-dimensional position $PS_T$ of the leading end portion of the treatment tool 6 by an offset calculation operation. The position sensor 8 sends the calculated three-dimensional position data $PS_T$ and three-dimensional posture data $DS_T$ of the treatment tool 6 to the image processing workstation 9 through a USB interface.

The image processing workstation 9 is a computer including a known hardware configuration, such as a CPU, a main storage device, a supplementary storage device, an input output interface, a communication interface, and a data bus. An input device (a pointing device, a keyboard, and the like) and the WS display 10 are connected to the image processing workstation 9. Further, the image processing workstation 9 is connected to the digital processor 2 and the modality 5 through LAN. The image processing workstation 9 is connected to the position sensor 8 by USB. Further, a known operating system, various kinds of application software, and the like have been installed in the image processing workstation 9. Further, an application for executing the endoscope observation assistance processing of the present invention has been installed in the image processing workstation 9. These kinds of software may be installed from a recording medium, such as a CD-ROM. Alternatively, the software may be downloaded from a storage device of a server connected through a network, such as the Internet, and installed.

Figure 2:
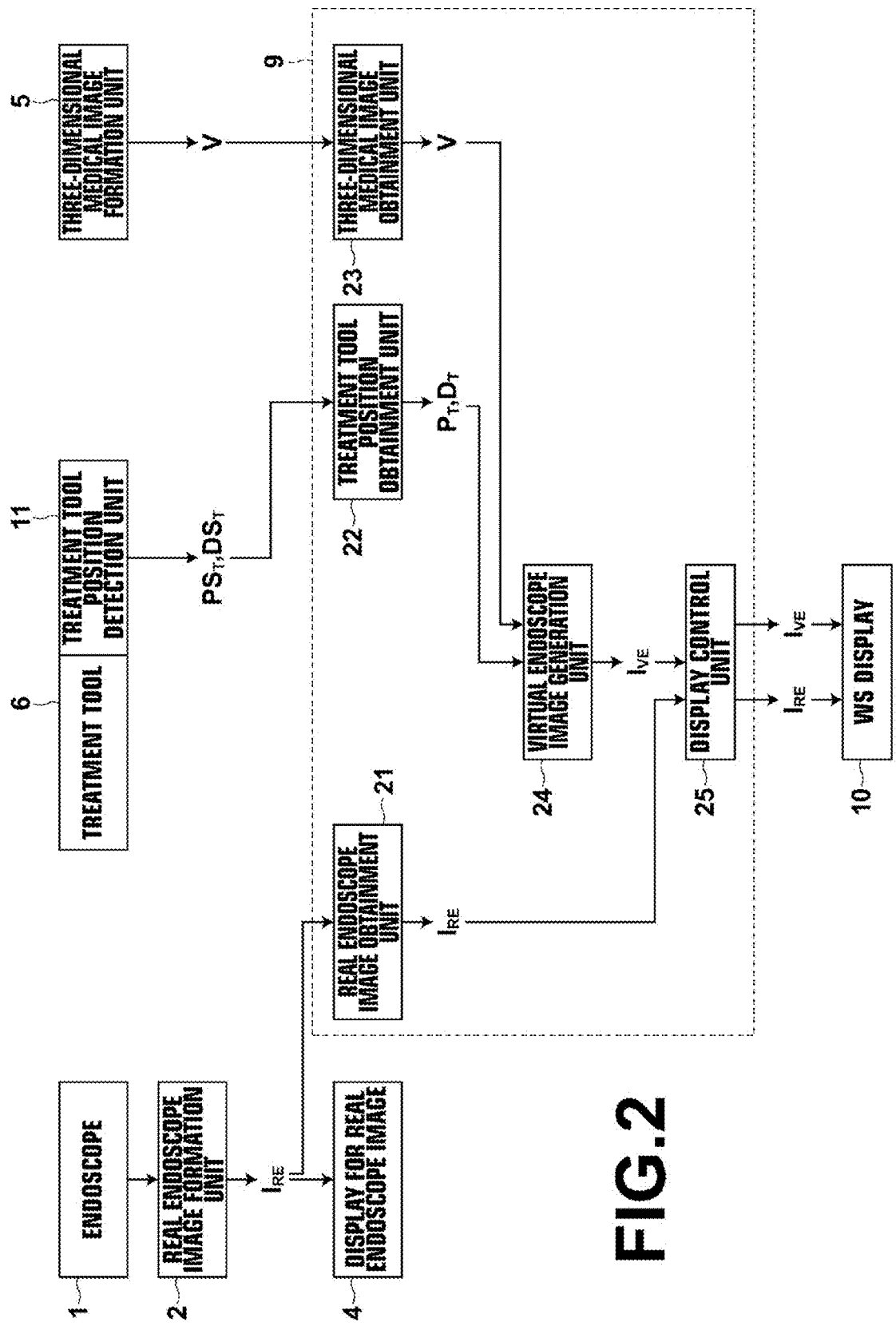
FIG. 2 is a functional block diagram illustrating the endoscope observation assistance system according to the first embodiment of the present invention.

FIG. 2 is a block diagram illustrating the endoscope observation assistance system according to the first embodiment of the present invention, and the system is divided at a function level. As illustrated in FIG. 2, the endoscope observation assistance system according to the first embodiment of the present invention includes an endoscope 1, a real endoscope image formation unit 2, a display 4 for a real endoscope image, a three-dimensional medical image formation unit 5, a WS display 10, a treatment tool position detection unit 11, a real endoscope image obtainment unit 21, a treatment tool position obtainment unit 22, a three-dimensional medical image obtainment unit 23, a virtual endoscope image generation unit 24, and a display control unit 25. When a hardware device illustrated in FIG. 1 and a functional block illustrated in FIG. 2 have substantially one-to-one correspondence, the same sign is assigned to them. Specifically, the function of the real endoscope image formation unit 2 is realized by the digital processor illustrated in FIG. 1. The function of the three-dimensional medical image formation unit 5 is realized by the modality illustrated in FIG. 1. Meanwhile, the function of the treatment tool position detection unit 11 is realized by the marker 7a for a treatment tool and the position sensor 8. Further, the image processing workstation 9 is represented by a broken line frame, and the function of each processing unit in the broken line frame is realized by executing a predetermined program at the image processing workstation 9. Further, real endoscope image $I_{RE}$, treatment tool detection position $PS_T$, treatment tool detection posture $DS_T$, treatment tool position $P_T$, treatment tool posture $D_T$, three-dimensional medical image V, and virtual endoscope image $I_{VE}$ are data that are read from or written in a predetermined memory area of the image processing workstation 9 by the processing units in the broken line frame, respectively.

Next, an operation performed by a user in the endoscope observation assistance system according to the first embodiment of the present invention, and a flow of processing performed in each of the aforementioned processing units will be schematically described by using a flow chart illustrated in FIG. 3.

First, the inside of the abdominal cavity of a subject to be examined is imaged by the three-dimensional medical image formation unit 5 before observation of the abdominal cavity of the subject to be examined by the endoscope 1, and three-dimensional medical image V is formed. In the image processing workstation 9, the three-dimensional medical image obtainment unit 23 obtains the three-dimensional medical image V formed by the three-dimensional medical image formation unit 5 (#2).

Next, as written on the right side of the flow chart illustrated in FIG. 3, during an endoscopic surgery performed on a structure of interest, in other words, during observation of the abdominal cavity of a subject to be examined by the endoscope 1 until observation ends (#12; YES), the real endoscope image formation unit 2 repeats, at a predetermined frame rate, formation of real endoscope image $I_{RE}$ by the endoscope 1 inserted into the body cavity, and the formed real endoscope image $I_{RE}$ is displayed in real time on the display 4 for a real endoscope image as a through dynamic image. Further, the treatment tool position detection unit 11 repeats, in real time, detection of position $PS_T$ and posture $DS_T$ of the treatment tool 6 inserted into the body cavity with predetermined time intervals.

In the image processing workstation 9, the real endoscope image obtainment unit 21 obtains real endoscope image $I_{RE}$ formed by the real endoscope image formation unit 2 (#4). At substantially the same timing as this, the treatment tool position obtainment unit 22 obtains treatment tool detection position $PS_T$ and treatment tool detection posture $DS_T$ detected by the treatment tool position detection unit 11. Further, the treatment tool position obtainment unit 22 transforms the obtained treatment tool detection position $PS_T$ and treatment tool detection posture $DS_T$ to a position and a posture in the coordinate system of three-dimensional medical image V, and outputs the obtained treatment tool position $P_T$ and posture $D_T$ (#6).

Further, the virtual endoscope image generation unit 24 obtains angle $A_E$ of view of the endoscope 1 from a predetermined memory area in the image processing workstation 9.

The virtual endoscope image generation unit 24 receives three-dimensional medical image V obtained by the three-dimensional medical image obtainment unit 23, as an input, and generates virtual endoscope image $I_{VE}$ the viewpoint of which is treatment tool position $P_T$ obtained by the treatment tool position obtainment unit 22. Further, treatment tool posture $D_T$, in other words, a direction in which the treatment tool moves straight forward is a visual line at the center of the field of view of the virtual endoscope (#8).

Further, the display control unit 25 makes the WS display 10 display the real endoscope image $I_{RE}$ obtained by the real endoscope image obtainment unit 21 and virtual endoscope image $I_{VE}$ generated by the virtual endoscope image generation unit 24 (#10).

In the image processing workstation 9, unless an instruction operation for ending observation is performed (#12; No), obtainment of new real endoscope image $I_{RE}$ (#4), obtainment of treatment tool position $P_T$ and treatment tool posture $D_T$ at that time (#6), generation of virtual endoscope image $I_{VE}$ (#8), update of display of the real endoscope image $I_{RE}$ and the virtual endoscope image $I_{VE}$ (#10) are repeated. Accordingly, real endoscope images $I_{RE}$ and virtual endoscope images $I_{VE}$ are continuously displayed on the WS display 10 in such a manner that they are temporally synchronized with each other. Meanwhile, when an instruction operation for ending observation is performed (#12; Yes), the image processing workstation 9 ends the repeated processing of steps #4 through #10.

Next, processing performed at each processing unit of the image processing workstation 9 will be described in detail.

The real endoscope image obtainment unit 21 is a communication interface for receiving real endoscope image $I_{RE}$ by communication with the real endoscope image formation unit (digital processor) 2. The real endoscope image obtainment unit 21 stores the real endoscope image $I_{RE}$ in a predetermined memory area of the image processing workstation 9. The real endoscope image $I_{RE}$ is transferred from the real endoscope image formation unit 2 based on a request from the real endoscope image obtainment unit 21.

The treatment tool position obtainment unit 22 has a function as a communication interface for obtaining treatment tool detection position $PS_T$ and treatment tool detection posture $DS_T$ by communication with the treatment tool position detection unit 11. Further, the treatment tool position obtainment unit 22 has a function of transforming the obtained treatment tool detection position $PS_T$ and treatment tool detection posture $DS_T$ in the three-dimensional coordinate system of the position sensor 8 to treatment tool position $P_T$ and treatment tool posture $D_T$ represented by coordinate values in a three-dimensional coordinate system of three-dimensional medical image V. Further, the treatment tool position obtainment unit 22 stores the treatment tool position $P_T$ and the treatment tool posture $D_T$ in a predetermined memory area of the image processing workstation 9. In the former communication interface function, the treatment tool detection position $PS_T$ and the treatment tool detection posture $DS_T$ are obtained from the treatment tool position detection unit 11 based on a request from the treatment tool position obtainment unit 22. In the latter coordinate transformation function, rotation amounts of coordinate axes should be obtained in advance based on a corresponding relationship between the direction of each coordinate axis in the three-dimensional coordinate system of the position sensor and the direction of each coordinate axis in the three-dimensional coordinate system of three-dimensional medical image V. Further, the coordinate value of a position in a subject to be examined in the three-dimensional coordinate system of the position sensor 8, the position being corresponding to the origin of the three-dimensional medical image V, should be measured in advance. Further, parallel movement amounts of the coordinate axes of the two coordinate systems should be obtained based on the coordinate value of the origin. Then, it is possible to transform the treatment tool detection position $PS_T$ and the treatment tool detection posture $DS_T$ represented in the three-dimensional coordinate system of the position sensor 8 to treatment tool position $P_T$ and treatment tool posture $D_T$ represented by coordinate values in the three-dimensional coordinate system of the three-dimensional medical image V by using a matrix for performing rotation by the rotation amounts and parallel movement by the parallel movement amounts.

The three-dimensional medical image obtainment unit 23 has a communication interface function for receiving three-dimensional medical image V from the three-dimensional medical image formation unit 5. Further, the three-dimensional medical image obtainment unit 23 stores the three-dimensional medical image V in a predetermined memory area in the image processing workstation 9.

Figure 4A:
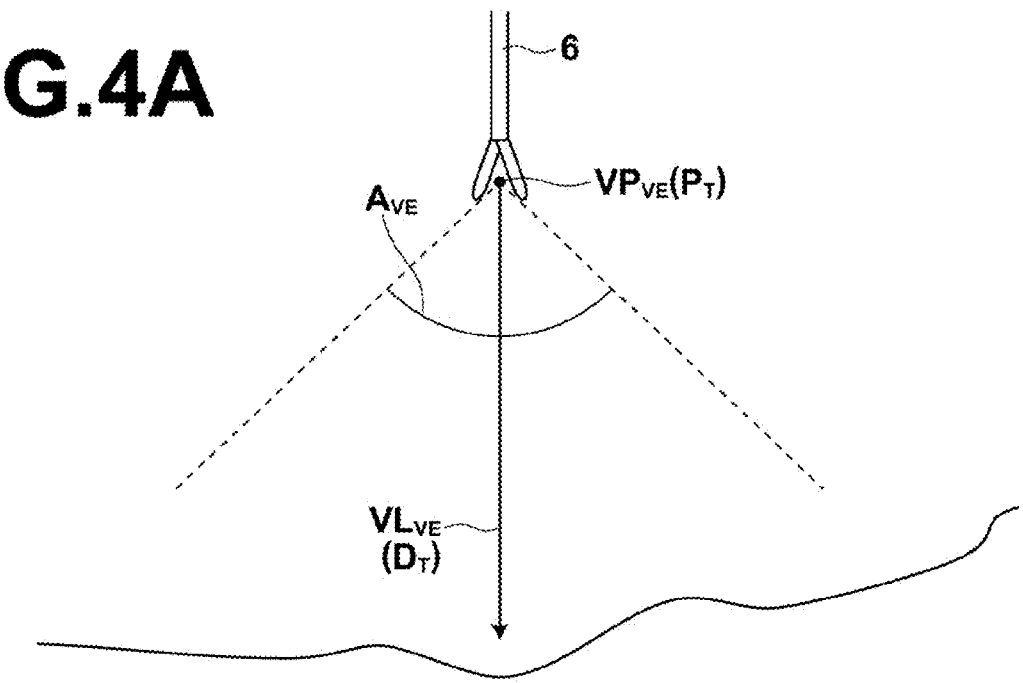
FIG. 4A is a schematic diagram illustrating an example of the position of a treatment tool, and the position of a viewpoint, a center visual line and an angle of view of a virtual endoscope in the first embodiment of the present invention.
Figure 4B:
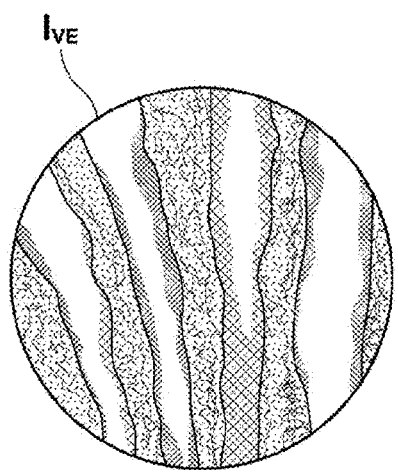
FIG. 4B is a schematic diagram illustrating an example of a virtual endoscope image in the first embodiment of the present invention.

The virtual endoscope image generation unit 24 receives the three-dimensional medical image V, as an input, and uses position $P_T$ of treatment tool 6, as viewpoint position $VP_{VE}$ of the virtual endoscope, as illustrated in FIG. 4A. Further, the virtual endoscope image generation unit 24 uses posture vector $D_T$ of the treatment tool 6, as visual line vector (hereinafter, referred to as center visual line vector) $VL_{VE}$ that passes the center of the field of view of the virtual endoscope image. Further, the virtual endoscope image generation unit 24 uses, as angle $A_{VE}$ of view, initial value $A_{VE0}$ of the angle of view of the virtual endoscope given by a processing parameter of a program and a setting file. Further, plural visual lines radially extending from the viewpoint position $VP_{VE}$ of the virtual endoscope are set within the range of the angle $A_{VE}$ of view, and virtual endoscope image $I_{VE}$ is generated by projecting voxel values on each of the visual lines by using a known volume rendering method by center projection. FIG. 4B is a schematic diagram illustrating the generated virtual endoscope image $I_{VE}$. Here, when volume rendering is performed, a color template in which colors and degrees of transparency are defined in advance so as to obtain an image representing substantially the same external view as that of each part in the abdominal cavity represented in the real endoscope image $I_{RE}$ is used.

The display control unit 28 generates a display screen in which the real endoscope image $I_{RE}$ and the virtual endoscope image $I_{VE}$ are arranged next to each other, and outputs the display screen to the WS display 10. Accordingly, the WS display 10 displays the display screen in which the real endoscope image $I_{RE}$ and the virtual endoscope image $I_{VE}$ are arranged next to each other.

As described above, in the first embodiment of the present invention, the virtual endoscope image generation unit 24 receives the three-dimensional medical image V, as an input, and uses position $P_T$ of the treatment tool 6, as viewpoint position $VP_{VE}$ of the virtual endoscope, and uses posture vector $D_T$ of the treatment tool 6, as center visual line vector $VL_{VE}$ of the virtual endoscope, and generates the virtual endoscope image $I_{RE}$. Further, the display control unit 28 displays the real endoscope image $I_{RE}$ and the virtual endoscope image $I_{VE}$ on the WS display 10. Here, the displayed virtual endoscope image $I_{VE}$ represents a state obtained by viewing the body cavity in a direction in which the treatment tool 6 moves straight forward from position $P_T$ of the treatment tool 6. In other words, the displayed virtual endoscope image $I_{VE}$ represents the body cavity as if the treatment tool 6 is an endoscope. Therefore, it is possible to observe the body cavity from the viewpoint of the treatment tool 6. If the virtual endoscope image $I_{VE}$ is used in combination with the real endoscope image $I_{RE}$, it is possible to observe the inside of the body cavity from many aspects.

At this time, the field of view of the virtual endoscope is changed in real time based on feedback of a result of detection of the position of the treatment tool 6 in real time by the treatment tool position detection unit 11, and virtual endoscope image $I_{VE}$ is continuously displayed. Therefore, it is possible to dynamically and more accurately recognize the movement condition of the treatment tool 6 in the body cavity.

Further, the real endoscope image formation unit 2 forms real endoscope image $I_{RE}$ representing the body cavity by imaging in real time by the endoscope 1, and real endoscope image $I_{RE}$ formed substantially at the same timing as detection of the position of the treatment tool 6 used at the time of generation of the virtual endoscope image $I_{VE}$ is displayed. Therefore, the real endoscope image $I_{RE}$ and the virtual endoscope image $I_{VE}$ represent the condition of the inside of the body cavity substantially at the same time, and real endoscope image $I_{RE}$ and the virtual endoscope image $I_{VE}$ are continuously displayed in such a manner that they are temporally synchronized with each other. At this time, the field of view of the real endoscope image $I_{RE}$ is changed in such a manner to be linked with an operation, such as the movement and rotation of the endoscope 1. Further, the field of view of the virtual endoscope image $I_{VE}$ is changed in such a manner to be linked with an operation, such as the movement and rotation of the treatment tool 6. As described above, in the first embodiment of the present invention, it is possible to observe the inside of the body cavity in real time by the real endoscope image $I_{RE}$ and the virtual endoscope image $I_{VE}$ in such a manner that they supplement each other.

Further, the virtual endoscope image generation unit 24 generates virtual endoscope image $I_{VE}$ by using a color template in which colors and degrees of transparency are defined in advance so as to obtain an image having substantially the same external view as that of each part in the abdominal cavity represented in the real endoscope image $I_{RE}$. Therefore, when the display control unit 25 displays the real endoscope image $I_{RE}$ and the virtual endoscope image $I_{VE}$ next to each other on the WS display 10, it is possible to observe the two images without experiencing any sense of incongruity.

In the above embodiment, it is desirable that the field of view of the endoscope 1 is supplemented with a wider range of angle by setting initial value $A_{VE0}$ of the angle of view of a virtual endoscope at an angle wider than the angle of view of the endoscope 1.

In the above embodiment, the field of view of the virtual endoscope is determined only based on position $P_T$ and posture $D_T$ of the treatment tool 6. Therefore, virtual endoscope image $I_{VE}$ does not always include a structure of interest in the body cavity. In some cases, it has been necessary to move the treatment tool 6 to check the positional relationship between the treatment tool 6 and the structure of interest and a state in which the treatment tool 6 becomes close to the structure of interest.

Figure 5:
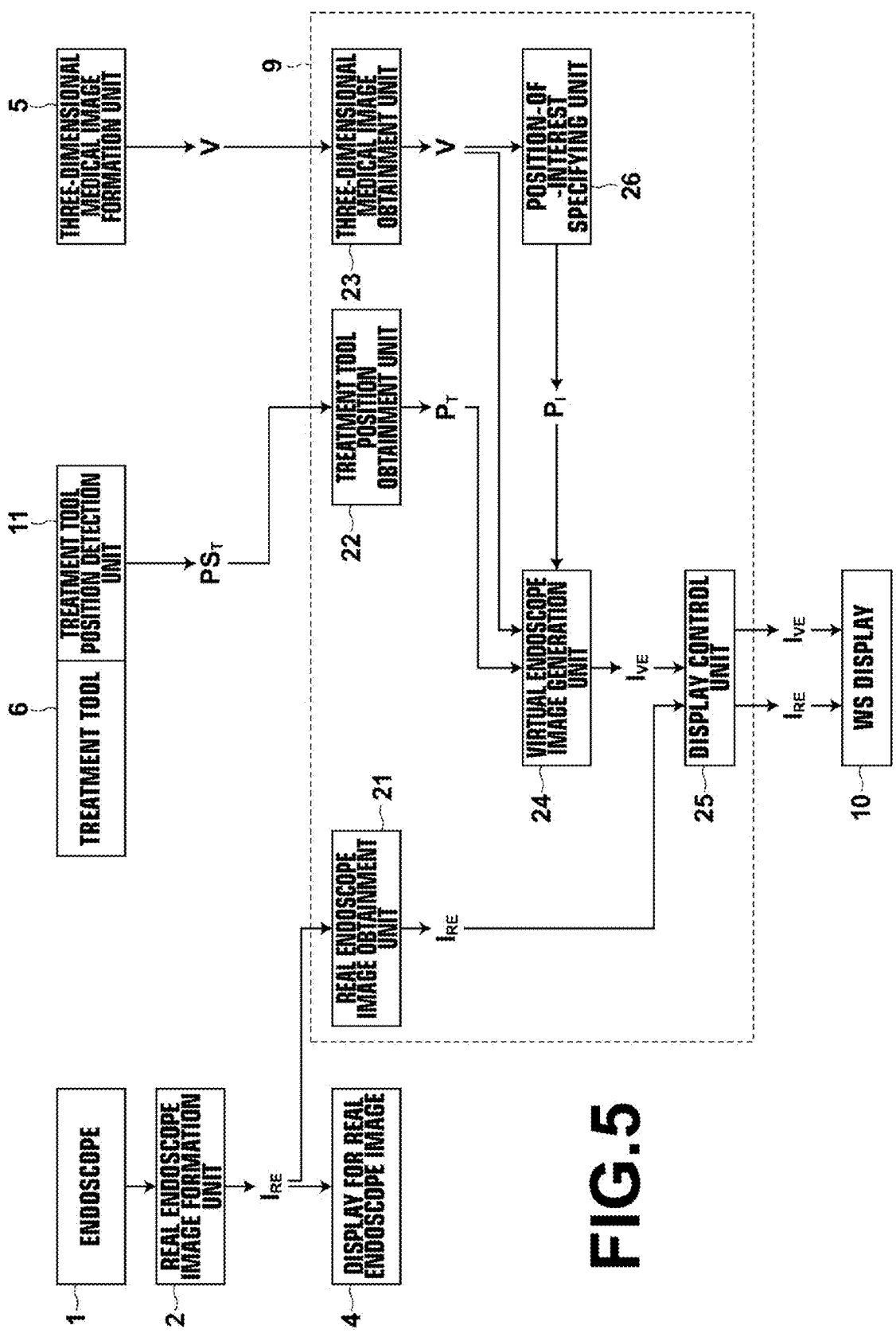
FIG. 5 is a functional block diagram illustrating the endoscope observation assistance system according to the second embodiment of the present invention.

Therefore, in a second embodiment of the present invention, the field of view of the virtual endoscope is determined based on the position of the treatment tool 6 and the position of the structure of interest. FIG. 5 is a functional block diagram of an endoscope observation assistance system in the second embodiment of the present invention. As illustrated in FIG. 5, a position-of-interest specifying unit 26 is provided in addition to the elements of the first embodiment.

FIG. 6 is a flow chart illustrating a flow of endoscope observation assistance processing in the second embodiment of the present invention. As illustrated in FIG. 6, after three-dimensional medical image V is obtained in step #2 of the first embodiment, the position-of-interest specifying unit 26 presents a user interface for receiving an operation for specifying a structure of interest (for example, a region on which a surgery is to be performed) in a body cavity represented in the three-dimensional medical image V obtained by the three-dimensional medical image obtainment unit 23. Further, the position-of-interest specifying unit 26 specifies, based on the obtained three-dimensional medical image V, position $P_T$ of the specified structure of interest in the three-dimensional medical image V (#3). After then, real endoscope image $I_{RE}$ is obtained in a similar manner to the first embodiment (#4). Here, as written on the right side of the flow chart, the treatment tool position detection unit 11 does not output treatment tool detection posture $DS_T$, and outputs only treatment tool detection position $PS_T$. Therefore, in step #6, the treatment tool position obtainment unit 22 obtains only treatment tool position $P_T$. After this, processing is similar to the first embodiment.

Next, the content of processing by each processing unit in the second embodiment of the present invention will be described in detail, and features different from the first embodiment will be mainly described.

The position-of-interest specifying unit 26 presents a user interface in a slice image representing a predetermined cross section generated from the three-dimensional medical image V by a known MPR method. The user interface receives an operation for specifying a structure of interest by using a pointing device or a keyboard of the image processing workstation 9. For example, when a structure of interest in the slice image is clicked by the pointing device, the position-of-interest specifying unit 26 identifies position $P_I$ of the structure of interest that has been specified by clicking in the three-dimensional medical image V, and stores the position $P_I$ in a predetermined memory area of the image processing workstation 9. Here, as the structure of interest, a region on which a surgery is to be performed, a region that requires caution in a surgery, or the like is specified as desired by a user.

As described above, the treatment tool position detection unit 11 does not output treatment tool detection posture $DS_T$. Further, the treatment tool position obtainment unit 22 also does not output treatment tool posture $D_T$.

Figure 7A:
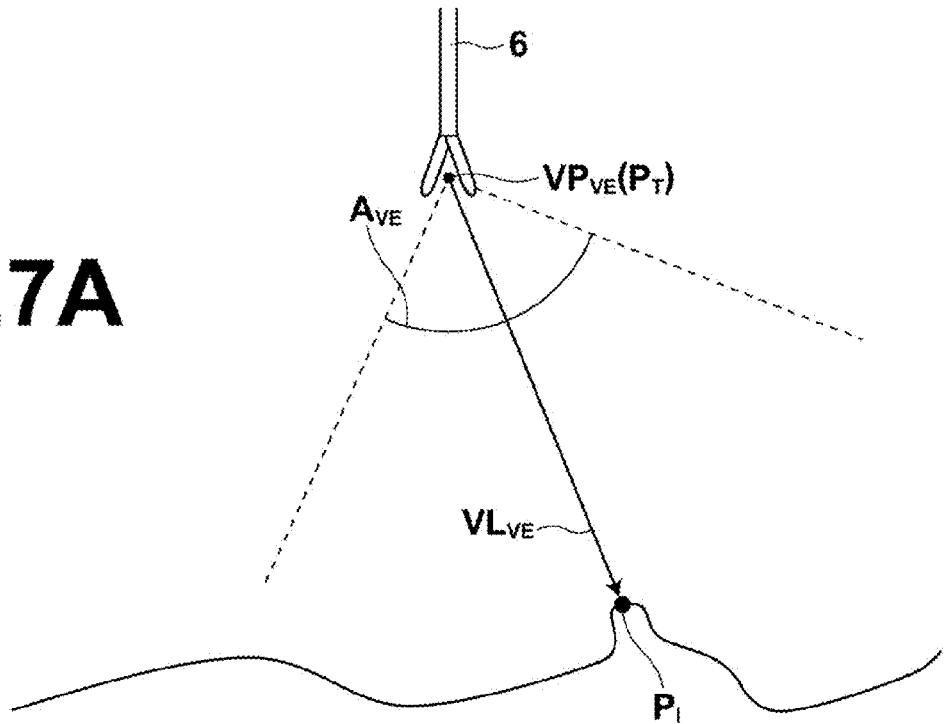
FIG. 7A is a schematic diagram illustrating an example of the position of a treatment tool, the position of a structure of interest, the position of a viewpoint, a center visual line and an angle of view of a virtual endoscope in the second embodiment of the present invention.

The virtual endoscope image generation unit 24 receives three-dimensional medical image V, as an input. Further, as illustrated in FIG. 7A, the virtual endoscope image generation unit 24 uses position $P_T$ of the treatment tool 6, as viewpoint position $VP_{VE}$ of the virtual endoscope. The virtual endoscope image generation unit 24 generates virtual endoscope image $I_{VE}$ by using a visual line directed from the position $P_T$ of the treatment tool 6 toward position $P_I$ of the structure of interest, as center visual line vector $VL_{VE}$ and by using initial value $A_{VE0}$ of the angle of view, as angle $A_{VE}$ of view.

Figure 7B:
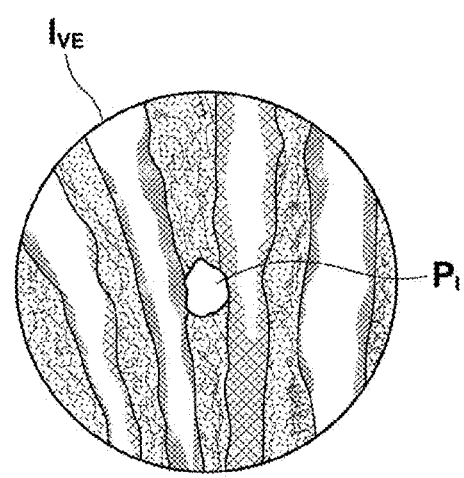
FIG. 7B is a schematic diagram illustrating an example of a virtual endoscope image in the second embodiment of the present invention.

As described above, in the second embodiment of the present invention, the virtual endoscope image $I_{VE}$ generated by the virtual endoscope image generation unit 24 is represented in such a manner that position $P_I$ of the structure of interest is at the center of the field of view, as illustrated in FIG. 7B. Therefore, the structure of interest is always included in the virtual endoscope image $I_{VE}$. Therefore, it is possible to more definitely recognize the positional relationship between the treatment tool 6 and the structure of interest and a state in which the treatment tool 6 becomes close to the structure of interest without operating the treatment tool 6.

However, in the virtual endoscope image $I_{VE}$ generated in the second embodiment, it is difficult to recognize a direction in which the treatment tool 6 moves straight forward.

Therefore, an embodiment in which both of a positional relationship or close proximity between the treatment tool 6 and the structure of interest and a direction in which the treatment tool 6 moves straight forward are easily recognizable will be described.

Figure 8:
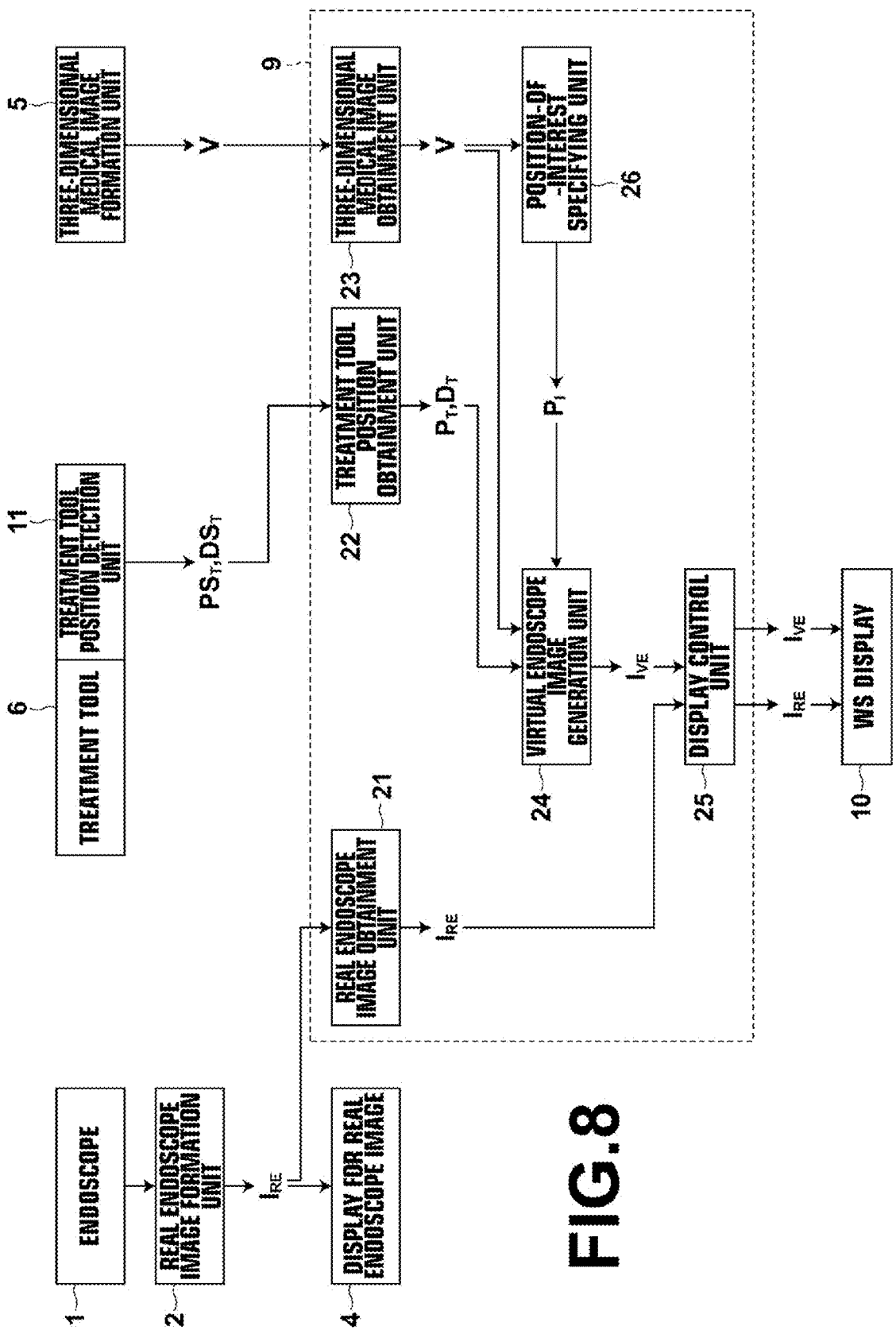
FIG. 8 is a functional block diagram illustrating the endoscope observation assistance system according to the third through seventh embodiments of the present invention.
Figure 9:
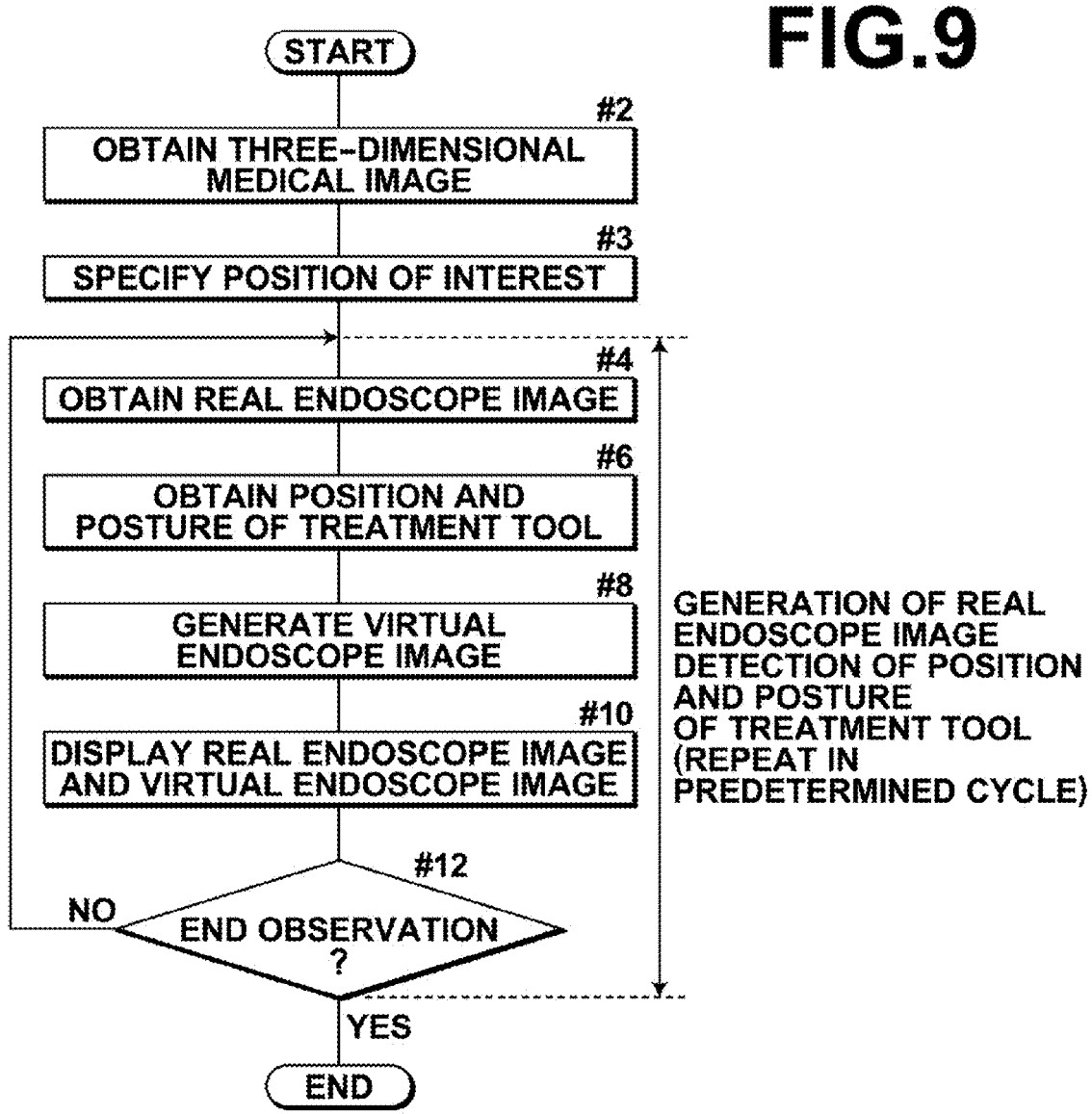
FIG. 9 is a flow chart illustrating a flow of endoscope observation assistance processing in the third through seventh embodiments of the present invention.

FIG. 8 is a functional block diagram illustrating an endoscope observation assistance system according to third through fifth embodiments of the present invention. As illustrated in FIG. 8, these embodiments differ from the second embodiment in that the treatment tool position detection unit 11 detects treatment tool detection posture $DS_T$, and that the treatment tool position obtainment unit 22 obtains treatment tool posture $D_T$. Similarly, in a flow chart illustrated in FIG. 9, these embodiments differ from the second embodiment in that posture $D_T$ of the treatment tool is obtained together with position $P_T$ of the treatment tool in step #6, and that not only position $PS_T$ of the treatment tool but also posture $DS_T$ of the treatment tool is detected while steps #4 through #10 are repeated.

Figure 10A:
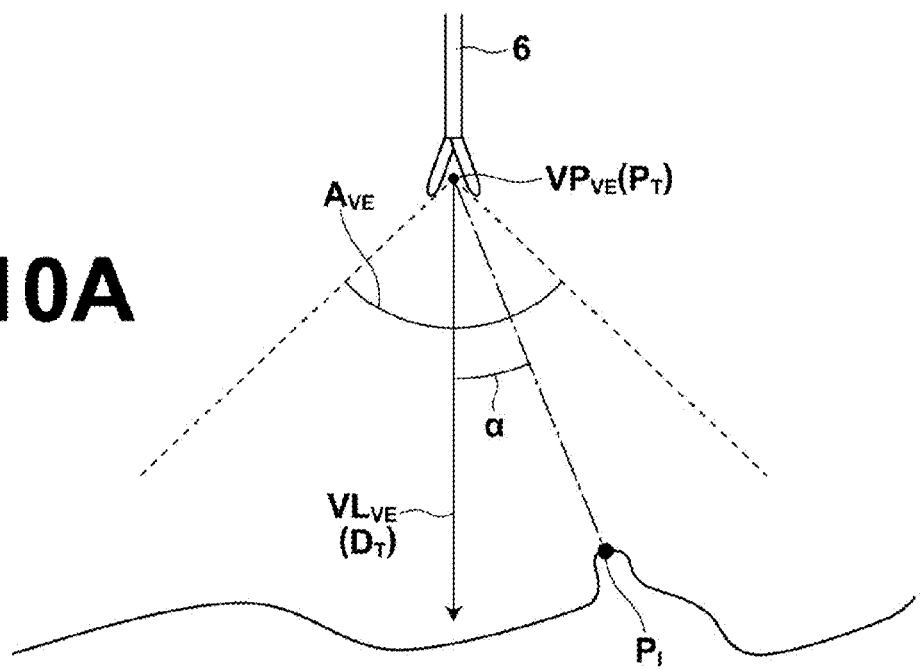
FIG. 10A is a schematic diagram illustrating an example of the position of a treatment tool, the position of a structure of interest, the position of a viewpoint, a center visual line and an angle of view of a virtual endoscope in the third embodiment of the present invention.

In the present embodiment, the virtual endoscope image generation unit 24 receives three-dimensional medical image V, as an input. Further, as illustrated in FIG. 10A, position $P_T$ of the treatment tool 6 is used as viewpoint position $VP_{VE}$ of a virtual endoscope, and posture vector $D_T$ of the treatment tool 6 is used as center visual line vector $VL_{VE}$. Further, virtual endoscope image $I_{VE}$ having angle $A_{VE}$ of view in such a manner that position $P_I$ of the structure of interest is included in the field of view of the virtual endoscope is generated. Here, for example, when an angle formed between a vector connecting viewpoint position $VP_{VE}$ of a virtual endoscope and position $P_I$ of a structure of interest and center visual line vector $VL_{VE}$ of the virtual endoscope is $\alpha$, angle $A_{VE}$ of view of the virtual endoscope is obtained by adding a constant to $2\alpha$, or by multiplying $2\alpha$ by a predetermined coefficient that is larger than 1.

Figure 10B:
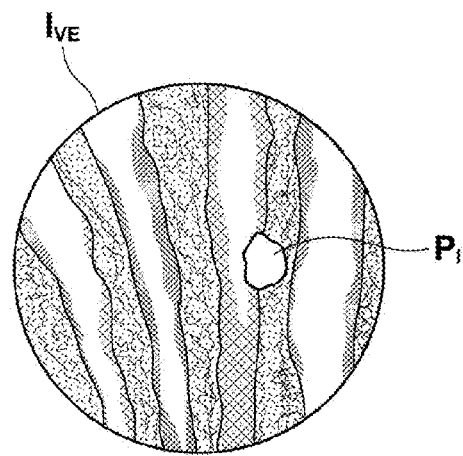
FIG. 10B is a schematic diagram illustrating an example of a virtual endoscope image in the third embodiment of the present invention.

As described above, in the third embodiment of the present invention, in the virtual endoscope image $I_{VE}$ generated by the virtual endoscope image generation unit 24, the direction of the center of the field of view represents a direction in which the treatment tool 6 moves straight forward, and a structure of interest is included in the field of view, as illustrated in FIG. 10B.

Figure 11A:
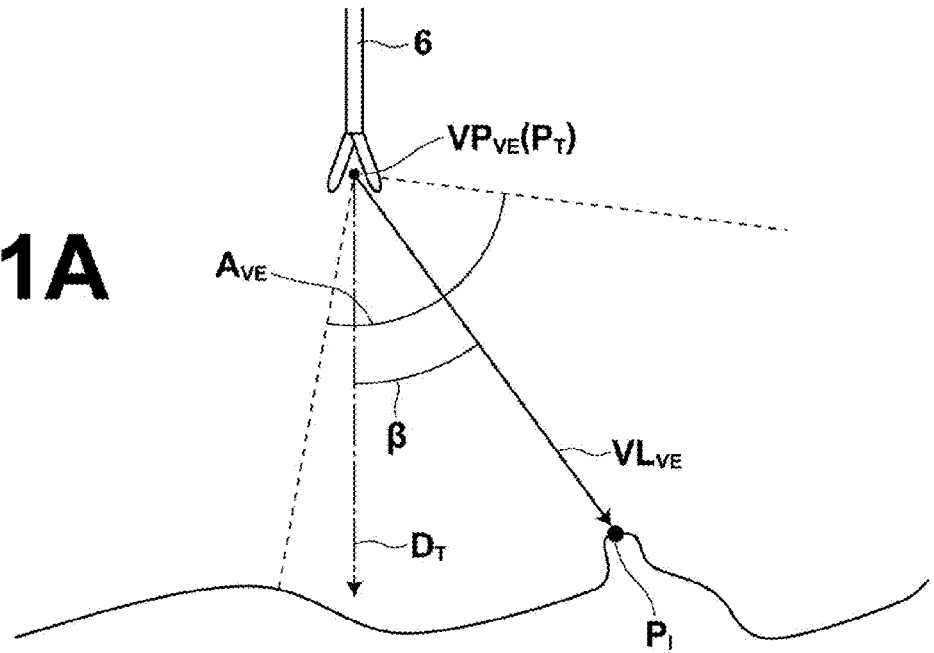
FIG. 11A is a schematic diagram illustrating an example of the position of a treatment tool, the position of a structure of interest, the position of a viewpoint, a center visual line and an angle of view of a virtual endoscope in the fourth embodiment of the present invention.

The fourth embodiment of the present invention is a modified example of a method for setting a field of view of a virtual endoscope. In the present embodiment, the virtual endoscope image generation unit 24 receives three-dimensional medical image V, as an input. Further, as illustrated in FIG. 11A, the virtual endoscope image generation unit 24 uses position $P_T$ of the treatment tool 6, as viewpoint position $VP_{VE}$ of a virtual endoscope. The virtual endoscope image generation unit 24 generates virtual endoscope image $I_{VE}$ by using a visual line directed from the position $P_T$ of the treatment tool 6 toward position $P_I$ of the structure of interest, as center visual line vector $VL_{VE}$. The virtual endoscope image generation unit 24 generates the virtual endoscope image $I_{VE}$ having angle $A_{VE}$ of view in such a manner that posture vector $D_T$ of the treatment tool 6 is included in the field of view of the virtual endoscope. Here, for example, when an angle formed between posture vector $D_T$ and center visual line vector $VL_{VE}$ of the virtual endoscope is $\beta$, angle $A_{VE}$ of view of the virtual endoscope is obtained by adding a constant to $2\beta$, or by multiplying $2\beta$ by a predetermined coefficient that is larger than 1.

In the present embodiment, the virtual endoscope image generation unit 24 further calculates a position in virtual endoscope image $I_{VE}$ at which image information on posture vector $D_T$ is projected, and adds marker $AP_T$ (a star sign in FIG. 11B) that represents a direction in which the treatment tool 6 moves straight forward at the calculated position.

Figure 11B:
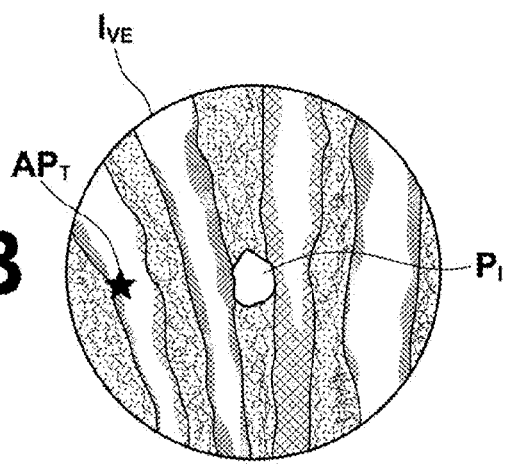
FIG. 11B is a schematic diagram illustrating an example of a virtual endoscope image in the fourth embodiment of the present invention.

As described above, in the fourth embodiment of the present invention, in the virtual endoscope image $I_{VE}$ generated by the virtual endoscope image generation unit 24, structure $P_I$ of interest is always present at the center of the field of view, and a direction in which the treatment tool 6 moves straight forward is indicated in the image, as illustrated in FIG. 11B.

Figure 12A:
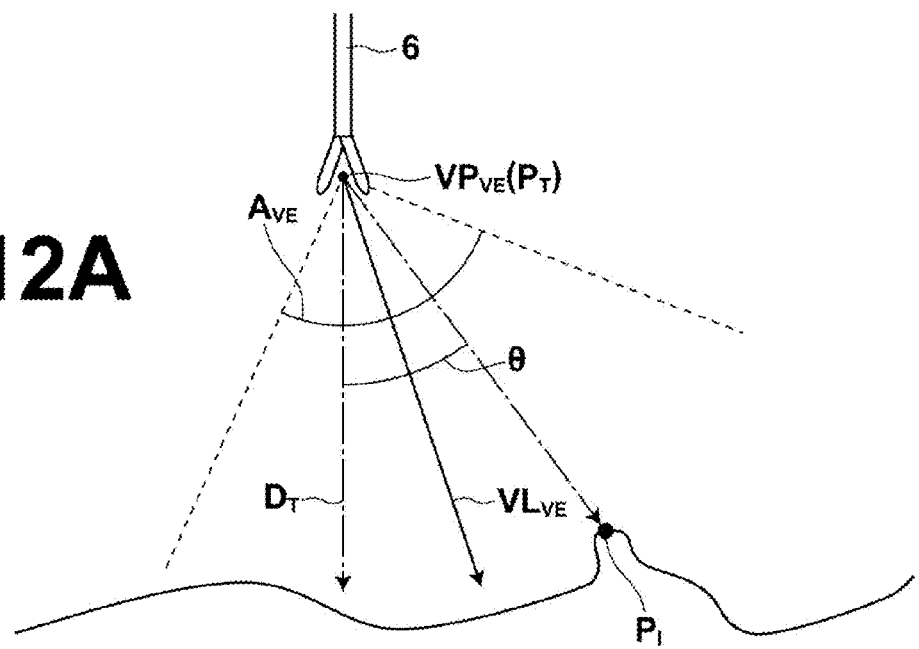
FIG. 12A is a schematic diagram illustrating an example of the position of a treatment tool, the position of a structure of interest, the position of a viewpoint, a center visual line and an angle of view of a virtual endoscope in the fifth embodiment of the present invention.

The fifth embodiment of the present invention is also a modified example of a method for setting a field of view of a virtual endoscope. In the present embodiment, the virtual endoscope image generation unit 24 receives three-dimensional medical image V, as an input. Further, as illustrated in FIG. 12A, the virtual endoscope image generation unit 24 uses position $P_T$ of the treatment tool 6, as viewpoint position $VP_{VE}$ of a virtual endoscope. The virtual endoscope image generation unit 24 generates virtual endoscope image $I_{VE}$ by using a visual line that divides angle $\theta$ formed between posture vector $D_T$ and a vector directed from position $P_T$ of the treatment tool 6 to position $P_I$ of the structure of interest, as center visual line vector $VL_{VE}$. The virtual endoscope image generation unit 24 generates the virtual endoscope image $I_{VE}$ having angle $A_{VE}$ of view in such a manner that posture vector $D_T$ and the structure of interest are included in the field of view of the virtual endoscope. Here, for example, angle $A_{VE}$ of view of the virtual endoscope may be obtained by adding a constant to $\theta$, or by multiplying $\theta$ by a predetermined coefficient that is larger than 1.

Figure 12B:
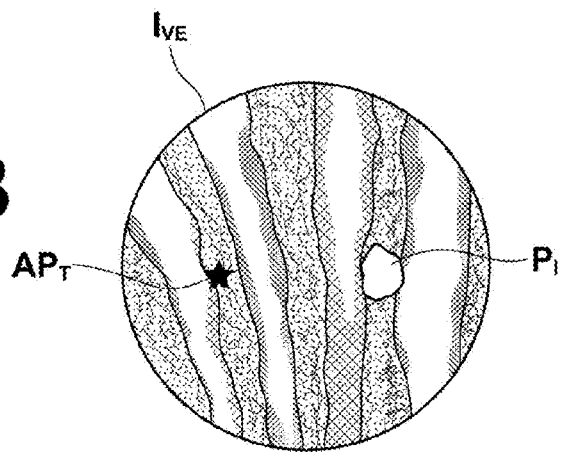
FIG. 12B is a schematic diagram illustrating an example of a virtual endoscope image in the fifth embodiment of the present invention.

Also in the present embodiment, the virtual endoscope image generation unit 24 further calculates a position in virtual endoscope image $I_{VE}$ at which image information on posture vector $D_T$ is projected, and adds marker $AP_T$ (a star sign in FIG. 12B) that represents a direction in which the treatment tool 6 moves straight forward at the calculated position.

As described above, in the fifth embodiment of the present invention, in the virtual endoscope image $I_{VE}$ generated by the virtual endoscope image generation unit 24, structure $P_I$ of interest is always present in the field of view, and a direction in which the treatment tool 6 moves straight forward is indicated in the image, as illustrated in FIG. 11B.

As described above, in the third through fifth embodiments of the present invention, the virtual endoscope image generation unit 24 generates virtual endoscope image $I_{VE}$ representing both of a direction in which the treatment tool 6 moves straight forward and the structure of interest. Therefore, it is possible to more easily and more definitely recognize both of the positional relationship or close proximity between the treatment tool 6 and the structure of interest and a direction in which the treatment tool 6 moves straight forward. Hence, it is possible to prevent a mistake in manual procedures during a surgery or an examination.

In each of the third through fifth embodiments, when the angle of view of a virtual endoscope is determined, initial value $A_{VE0}$ of angle of view that is wider than the angle of view of the endoscope 1 may be set in advance. When the value of the angle of view obtained in the aforementioned processing is less than the initial value $A_{VE0}$, the initial value $A_{VE0}$ may be used as angle $A_{VE}$ of view to make the angle $A_{VE}$ of view of the virtual endoscope wider than the angle of view of the endoscope 1. In contrast, when the obtained angle $A_{VE}$ of view is greater than or equal to a predetermined threshold value, it may be judged as an error in setting of an angle of view, and predetermined error processing (displaying a warning message to urge a user to stop processing, to change the posture of the treatment tool 6, to correct position $P_I$ of the structure of interest, or the like) may be performed. Further, initial value $A_{VE0}$ of the angle of view may be a value that is not larger than necessary, and angle $A_{VE}$ of view based on the aforementioned angles $\alpha$, $\beta$ and $\theta$ may be determined. Then, for example, when the structure of interest is located close to the center of the field of view of the virtual endoscope, it is possible to set a large magnification ratio by narrowing the angle $A_{VE}$ of view. Consequently, an image in the field of view of the virtual endoscope is enlarged, and observation becomes easy.

Further, a marker or the like may be added also at a position in virtual endoscope image $I_{VE}$ at which position $P_I$ of the structure of interest is projected. Alternatively, the position-of-interest specifying unit 24 may extract a region representing the whole structure of interest based on position $P_I$ of the structure of interest specified by a user. Further, the virtual endoscope image generation unit 27 should perform volume rendering on the region representing the whole structure of interest by using a color template that is different from a template used for other structures. Then, it is possible to represent the region of the structure of interest in the virtual endoscope image $I_{VE}$ illustrated in FIG. 10B and the like in a highly distinguishable manner. Therefore, the virtual endoscope image $I_{VE}$ becomes more easily observable. Here, in the aforementioned extraction of the region of the structure of interest, Japanese Unexamined Patent Publication No. 2008-245719, proposed by FUJIFILM Corporation, may be used for example. Specifically, setting of arbitrary point $P_I$ in the region of the structure of interest is received (hereinafter, this point will be referred to as a user setting point). Further, a three-dimensional presence range in which a lesion region may be present is determined by using information about the likely size of the lesion region that has been defined in advance. Further, a lesion region may be extracted, based on the set point and a point on the outside of the determined presence range, by using a region division method or the like, such as a graph cut method.

A sixth embodiment of the present invention is a modified example of volume rendering in the virtual endoscope image generation unit 24. The hardware configuration and the functional block of the endoscope observation assistance system, the flow of whole processing, and the like, which are not described in this modified example, are similar to those of the third embodiment.

Figure 13A:
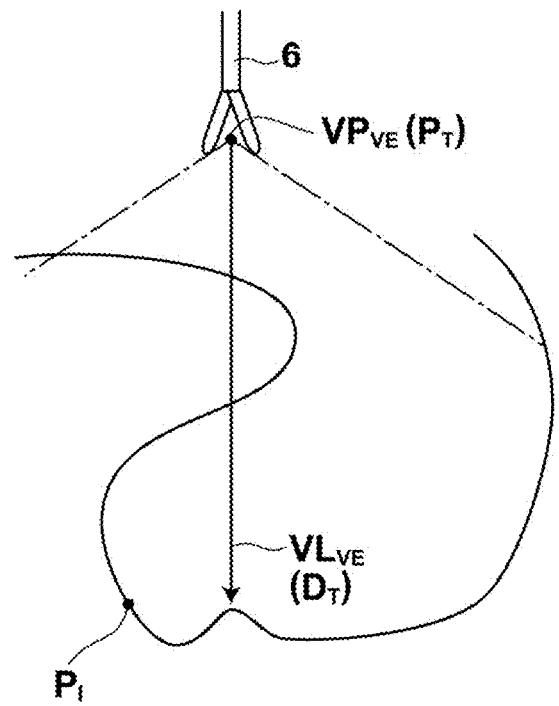
FIG. 13A is a schematic diagram illustrating an example of the position of a viewpoint, a center visual line and an angle of view of a virtual endoscope in the sixth embodiment of the present invention when another structure is present between a structure of interest and a treatment tool.
Figure 13B:
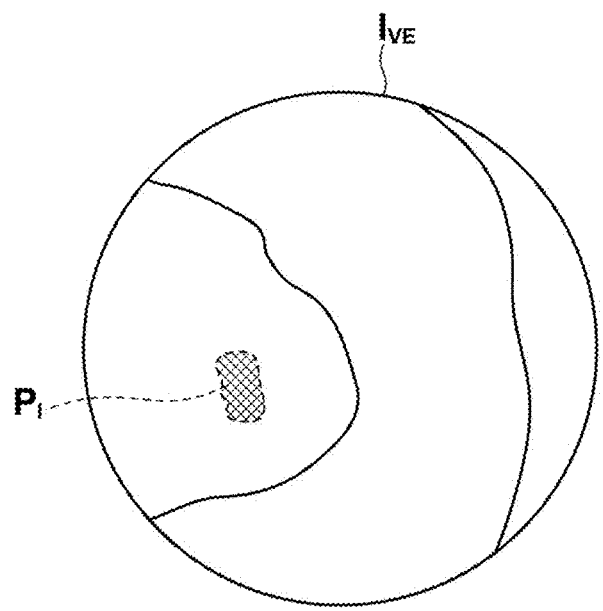
FIG. 13B is a schematic diagram illustrating an example of a virtual endoscope image in the sixth embodiment of the present invention.

FIG. 13A is a schematic diagram illustrating an example of a positional relationship between a structure of interest and a treatment tool 6. As illustrated in FIG. 13A, when another anatomical structure blocks a path from position $P_T$ of the treatment tool 6, which is a viewpoint of virtual endoscope image $I_{VE}$, to the structure of interest, if a color template has been defined in such a manner that a high opacity level is set for the anatomical structure, the structure of interest that is located on the back side of the anatomical structure is not rendered in the virtual endoscope image $I_{VE}$. Therefore, in the sixth embodiment, the virtual endoscope image generation unit 24 generates the virtual endoscope image $I_{VE}$ by using a color template in which an opacity level has been defined in such a manner that each part of the body cavity is displayed semi-transparently. Accordingly, in the generated virtual endoscope image $I_{VE}$, the anatomical structure present between position $P_I$ of the structure of interest and treatment tool position $P_T$ is displayed semi-transparently, as schematically illustrated in FIG. 13B. Consequently, position $P_I$ of the structure of interest present on the back side of the anatomical structure becomes recognizable. Especially, when the region of the structure of interest has been extracted, and a color template that is different from a color template used for other regions is used for the region of the structure of interest, as described in modified examples of the third through fifth embodiments, even if an anatomical structure is present between the position $P_I$ of the structure of interest and treatment tool position $P_T$, it is possible to represent the whole region of the structure of interest in a highly recognizable manner. The real endoscope image formation unit 2 cannot form an image in which an anatomical structure in the abdominal cavity is displayed semi-transparently as described above. Therefore, use of the virtual endoscope image $I_{VE}$ in which the anatomical structure is displayed semi-transparently to supplement the real endoscope image $I_{VE}$ is extremely valuable in practical use.

A seventh embodiment of the present invention is a modified example of volume rendering in the virtual endoscope image generation unit 24. The hardware configuration and the functional block of the endoscope observation assistance system, the flow of whole processing, and the like, which are not described in this modified example, are similar to those of the third embodiment.

Figure 14A:
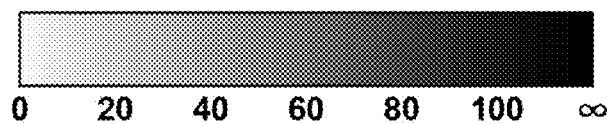
FIG. 14A is a schematic diagram illustrating an example of a color template for changing the display color of a virtual endoscope image based on a distance from a viewpoint to a surface of an anatomical structure in an abdominal cavity in the seventh embodiment of the present invention.
Figure 14B:
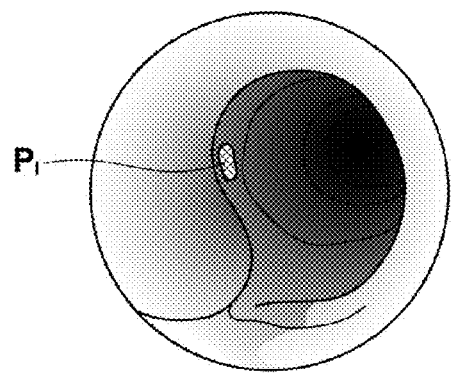
FIG. 14B is a schematic diagram illustrating an example of a virtual endoscope image the display color of which has been changed based on a distance from a viewpoint in the seventh embodiment of the present invention.

FIG. 14A is a schematic diagram illustrating an example of a color template used in the seventh embodiment of the present invention. As illustrated in FIG. 14A, this color template is defined in such a manner to change the color of the virtual endoscope image $I_{VE}$ based on a distance from the position $P_T$ of the treatment tool 6 (same as viewpoint position $P_{VE}$ of the virtual endoscope) to a surface of a structure in the abdominal cavity. For example, the virtual endoscope image generation unit 24 detects, as a surface of a structure in the abdominal cavity, a position at which a voxel value sharply changes by a predetermined threshold value or more, or a position at which a voxel value becomes a predetermined threshold value or more on each visual line when center projection is performed. Further, the virtual endoscope image generation unit 24 calculates a distance from position $P_T$ of the treatment tool 6 to the surface of the structure in the abdominal cavity, and determines a pixel value of the detected surface of the structure in the virtual endoscope image $I_{VE}$ by using this color template. Then, as schematically illustrated in FIG. 14B, the color of the surface of the structure is lighter as the distance from the position $P_T$ of the treatment tool 6 is shorter and the color of the surface of the structure is darker as the distance from the position $P_T$ of the treatment tool 6 is longer in the generated virtual endoscope image $I_{VE}$. When the virtual endoscope image $I_{VE}$ is generated in such a manner, it is possible to supplement the virtual endoscope image $I_{VE}$, which tends not to give perspective, with a sense of perspective. Therefore, it becomes possible to more easily recognize a state in which the treatment tool 6 becomes close to a structure in the abdominal cavity (including a structure of interest).

Figure 15:
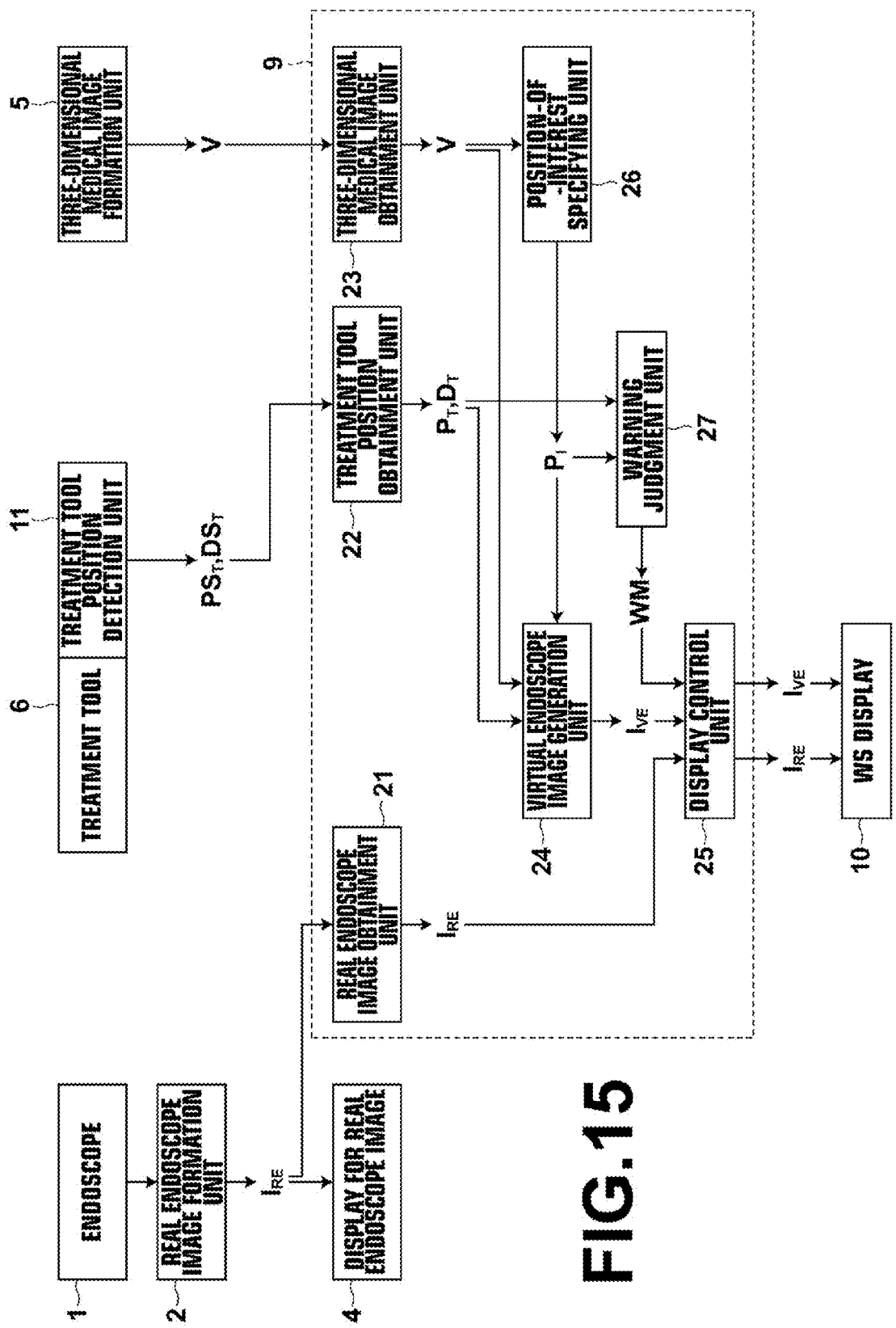
FIG. 15 is a functional block diagram illustrating the endoscope observation assistance system according to the eighth embodiment of the present invention.

In an eighth embodiment of the present invention, a warning judgment unit 27 is added to the third embodiment, as illustrated in a functional block diagram of FIG. 15. The hardware configuration of the endoscope observation assistance system is similar to the third embodiment.

The warning judgment unit 27 is a processing unit implemented in the image processing workstation 9. The warning judgment unit 27 calculates a distance between position $P_T$ of the treatment tool 6 and position $P_I$ of the structure of interest. When the calculated distance is less than a predetermined threshold value, in other words, when the treatment tool 6 is intolerably close to the structure of interest, the warning judgment unit 27 outputs warning message WM.

Figure 16:
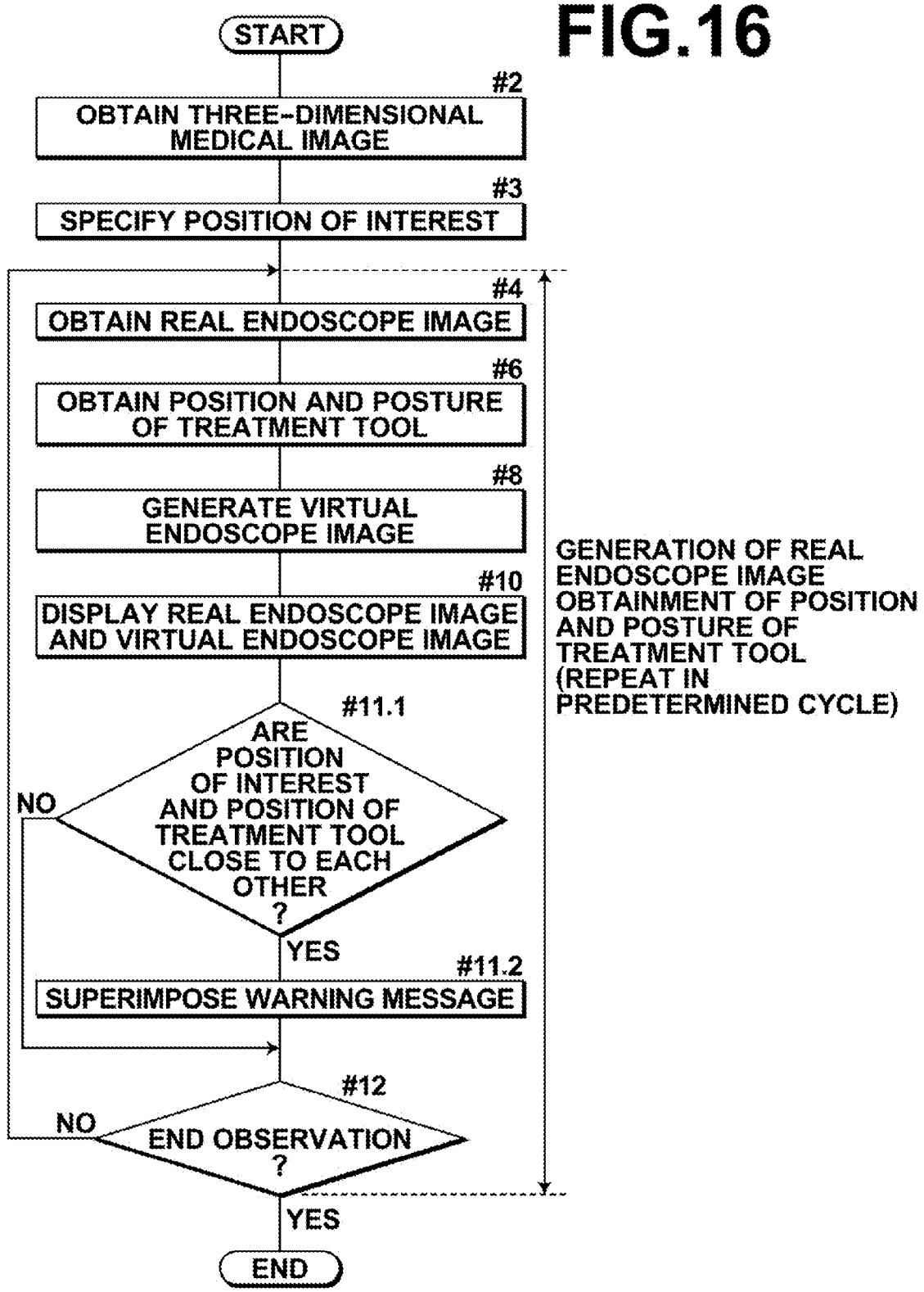
FIG. 16 is a flow chart illustrating a flow of endoscope observation assistance processing in the eighth embodiment of the present invention.
Figure 17:
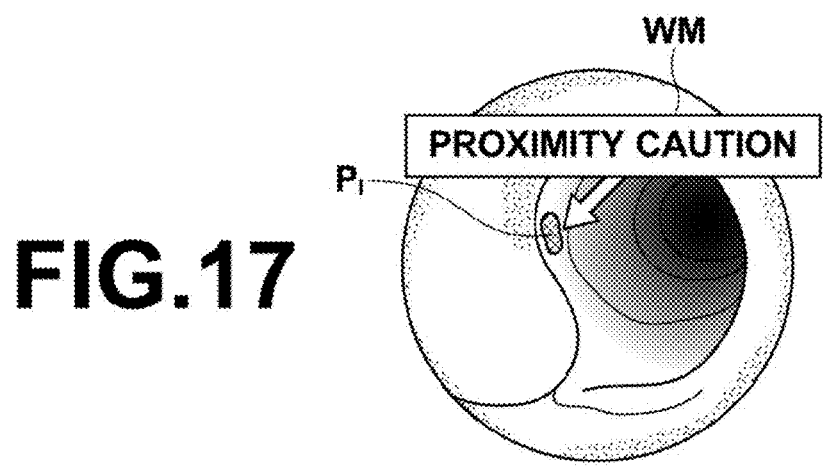
FIG. 17 is a schematic diagram illustrating an example of a warning displayed in the eighth embodiment of the present invention.

FIG. 16 is a flow chart illustrating a flow of endoscope observation assistance processing in the eighth embodiment of the present invention. As illustrated in FIG. 16, after real endoscope image $I_{RE}$ and virtual endoscope image $I_{VE}$ are displayed in step #10 of the third embodiment, the warning judgment unit 27 compares the distance and the threshold value with each other (#11.1). When the distance is less than the threshold value (#11.1; Yes), the warning judgment unit 27 outputs warning message WM. Further, as illustrated in an example of FIG. 17, the display control unit 25 superimposes an arrow mark with a comment of "PROXIMITY CAUTION" in the neighborhood of position $P_I$ of the structure of interest. Accordingly, it becomes possible to easily recognize a state in which the treatment tool 6 is abnormally close to the structure of interest. Hence, it is possible to prevent an erroneous operation of the treatment tool 6. Such warning display is especially effective when a blood vessel or the like that may cause serious bleeding by being damaged during a surgery has been specified as the structure of interest by the position-of-interest specifying unit 26.

A method for outputting the warning message to the outside may be the aforementioned method of superimposing the warning message on the virtual endoscope image $I_{VE}$. Alternatively, a warning sound or a warning voice may be output, or both of superposition of the warning message and output of the warning sound or the like may be performed. Further, a risk level judgment table that defines, based on the distances, risk levels in a stepwise manner may be prepared in advance, and the warning judgment unit 27 may determine a risk level based on the calculated distance with reference to the risk level judgment table. Further, the warning judgment unit 27 may output the value of the risk level as warning message WM. Further, the display control unit 25 may make the WS display 10 display an icon or the like based on the risk level.

Figure 18:
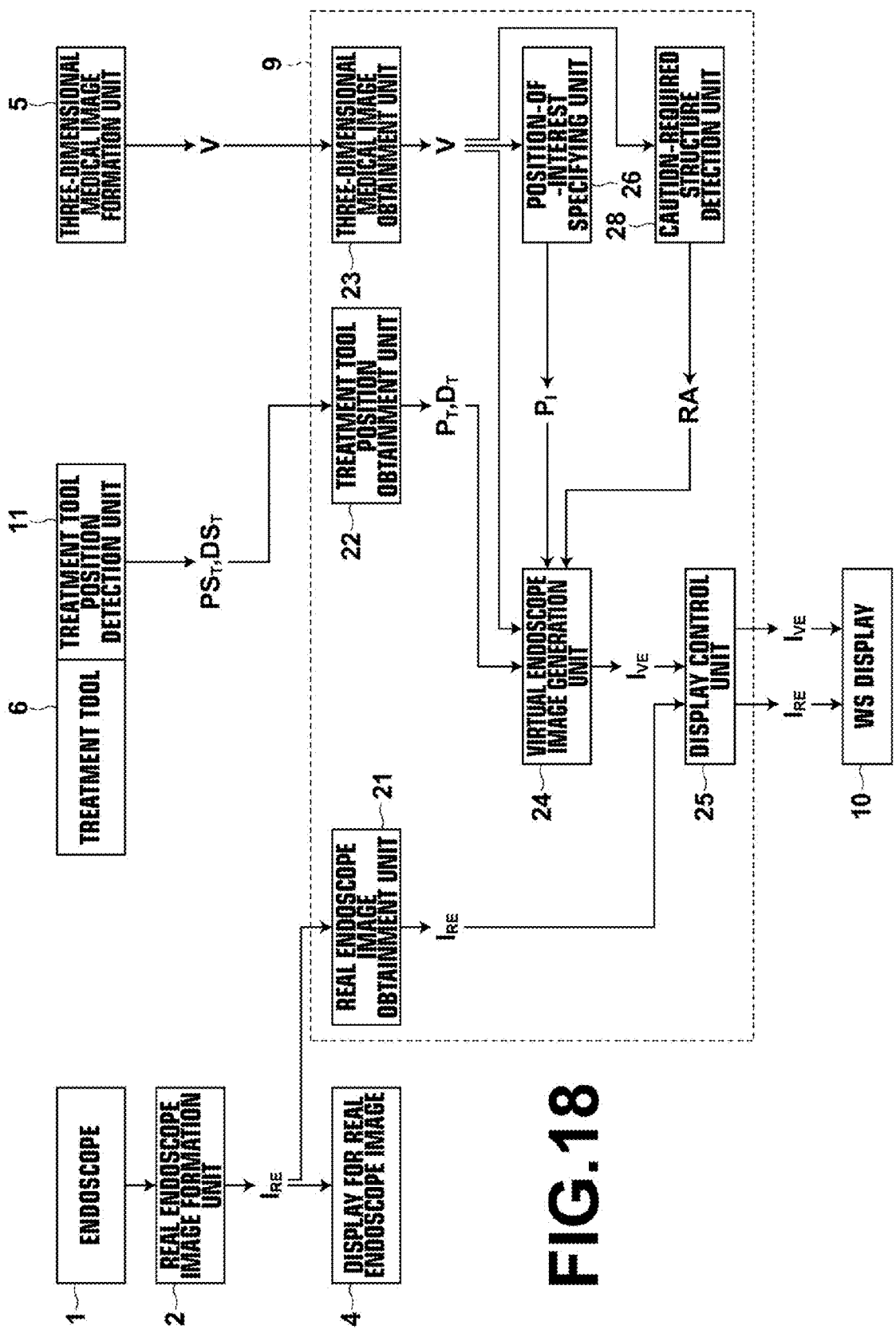
FIG. 18 is a functional block diagram illustrating the endoscope observation assistance system according to the ninth embodiment of the present invention.

In a ninth embodiment of the present invention, a caution-required structure detection unit 28 is added to the first embodiment, as illustrated in a functional block diagram of FIG. 18. The hardware configuration of the endoscope observation assistance system is similar to the third embodiment.

Figure 20A:
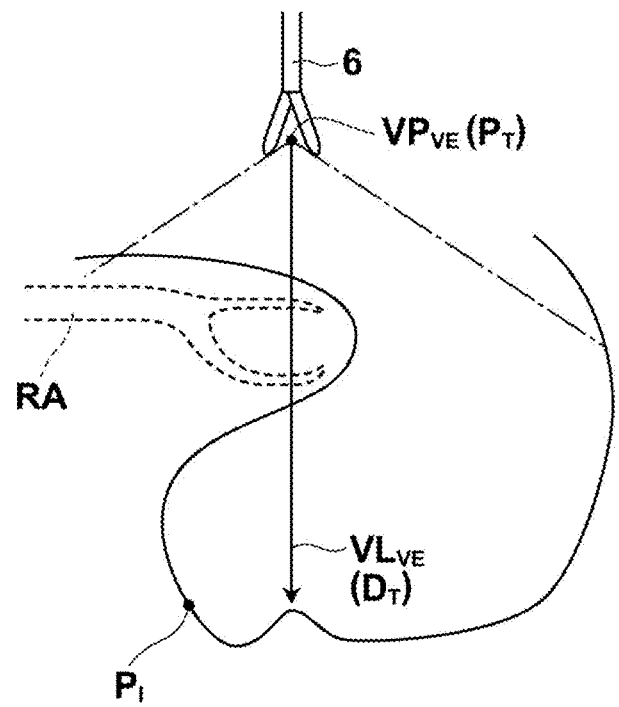
FIG. 20A is a schematic diagram illustrating an example of a positional relationship among a structure of interest, a caution-required structure and a treatment tool, and a field of view of a virtual endoscope in the ninth embodiment of the present invention.

The caution-required structure detection unit 28 is a processing unit implemented in the image processing workstation 9. The caution-required structure detection unit 28 receives three-dimensional medical image V, as an input, and detects caution-required structure region RA by using a known image recognition method. FIG. 20A is a schematic diagram illustrating an example of a positional relationship among the treatment tool 6, the structure of interest and the caution-required structure. In this example, the caution-required structure detection unit 28 detects caution-required blood vessel region RZ that is present on the back side of the abdominal wall by performing known blood vessel extraction processing.

Figure 19:
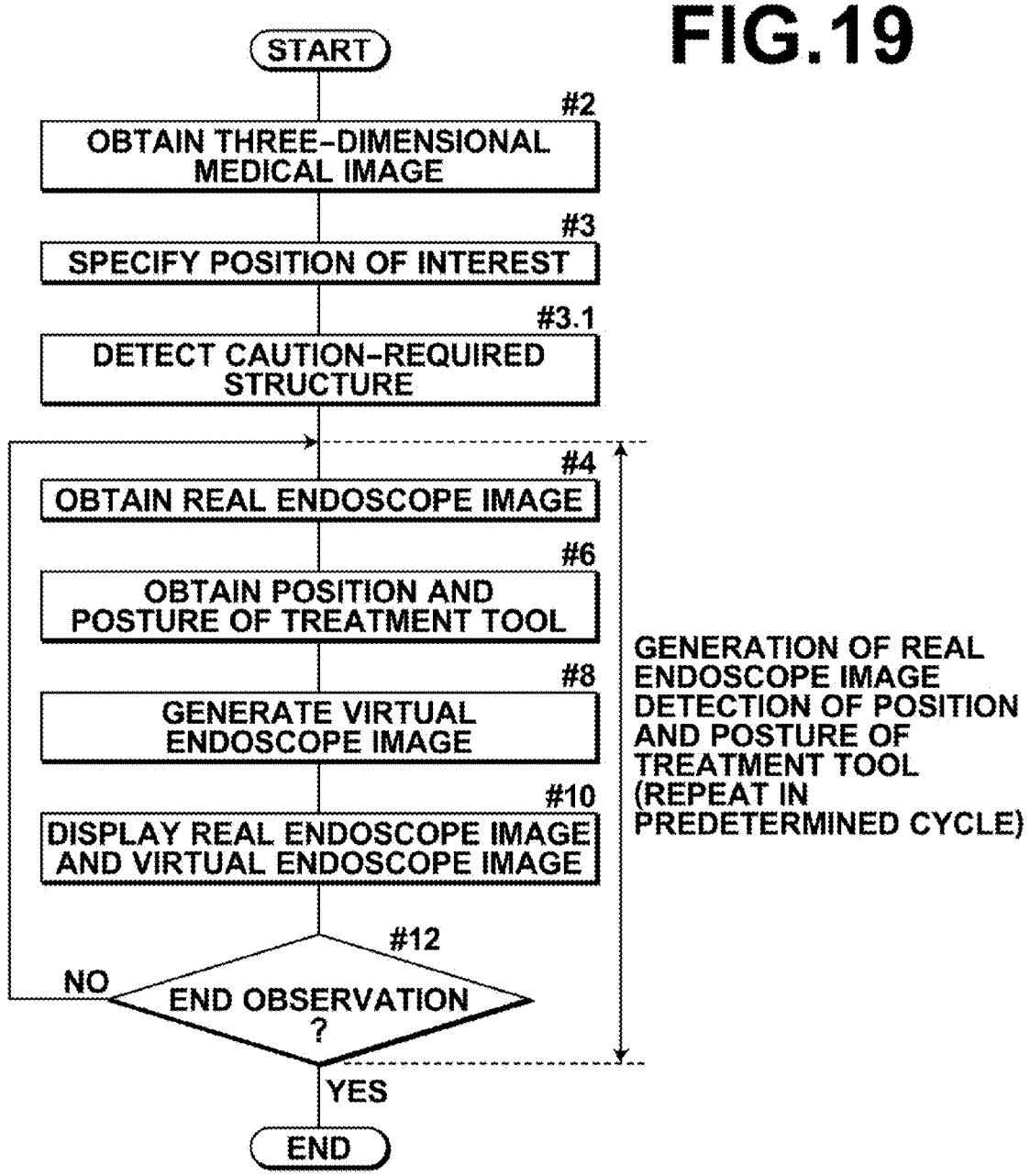
FIG. 19 is a flow chart illustrating a flow of endoscope observation assistance processing in the ninth embodiment of the present invention.
Figure 20B:
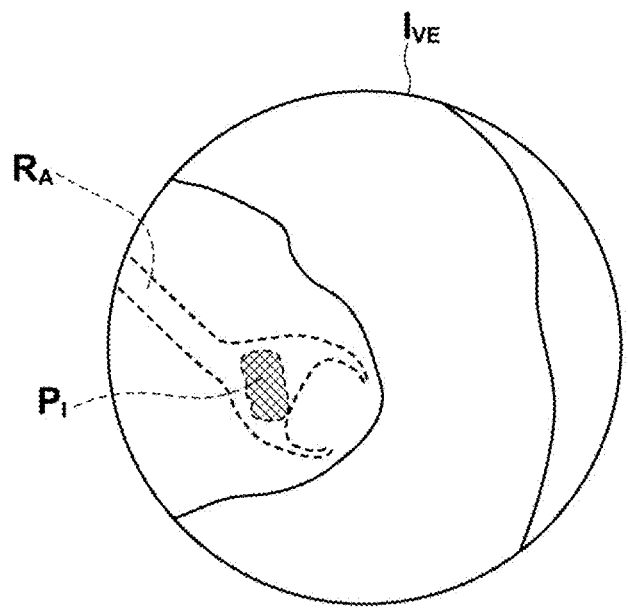
FIG. 20B is a schematic diagram illustrating an example of a virtual endoscope image in the ninth embodiment of the present invention.

FIG. 19 is a flow chart illustrating a flow of endoscope observation assistance processing in the ninth embodiment of the present invention. As illustrated in FIG. 19, after position $P_I$ of interest is specified in step #3 of the third embodiment, the caution-required structure detection unit 28 detects caution-required structure region RA (#3.1). Further, in step #8, the virtual endoscope image generation unit 24 generates virtual endoscope image $I_{VE}$ by using a color template that is defined in such a manner that the caution-required structure region RA is visually recognizable. FIG. 20B is a schematic diagram illustrating an example of the generated virtual endoscope image $I_{VE}$. The virtual endoscope image $I_{VE}$ illustrated in FIG. 20B is generated by using a color template in which colors and opacity degrees are defined in such a manner that pixels representing an abdominal wall are semi-transparent, and the recognition characteristic of pixels representing a blood vessel is higher. Accordingly, the recognition characteristic of the caution-required structure becomes higher. Therefore, it is possible to prevent an erroneous operation of the endoscope 1 and the treatment tool 6.

Further, the caution-required structure detection unit 28 may detect caution-required structure region RA by a manual operation of a user. Further, the caution-required structure detection unit 28 may superimpose a marker, such as an arrow, and an annotation, such as a text comment, for the caution-required structure region RA.

A tenth embodiment of the present invention generates a virtual endoscope image in such a manner that all of the structure of interest, the endoscope 1 and the posture vector of the treatment tool 6 are included in the field of view of the virtual endoscope image. As illustrated in the hardware configuration diagram of FIG. 21, a marker 7*b* for an endoscope is added to the first embodiment illustrated in FIG. 1.

The marker 7*b* for an endoscope and the position sensor 8 constitute a three-dimensional position measurement apparatus in a manner similar to the marker 7*a* for a treatment tool. The marker 7*b* for an endoscope is provided in the vicinity of a handle part of the endoscope 1. The position sensor 8 detects the three-dimensional position of the marker 7*b* with predetermined time intervals. Further, it is possible to calculate three-dimensional position $PS_E$ of the leading end of the endoscope 1 by off set calculation.

Figure 21:
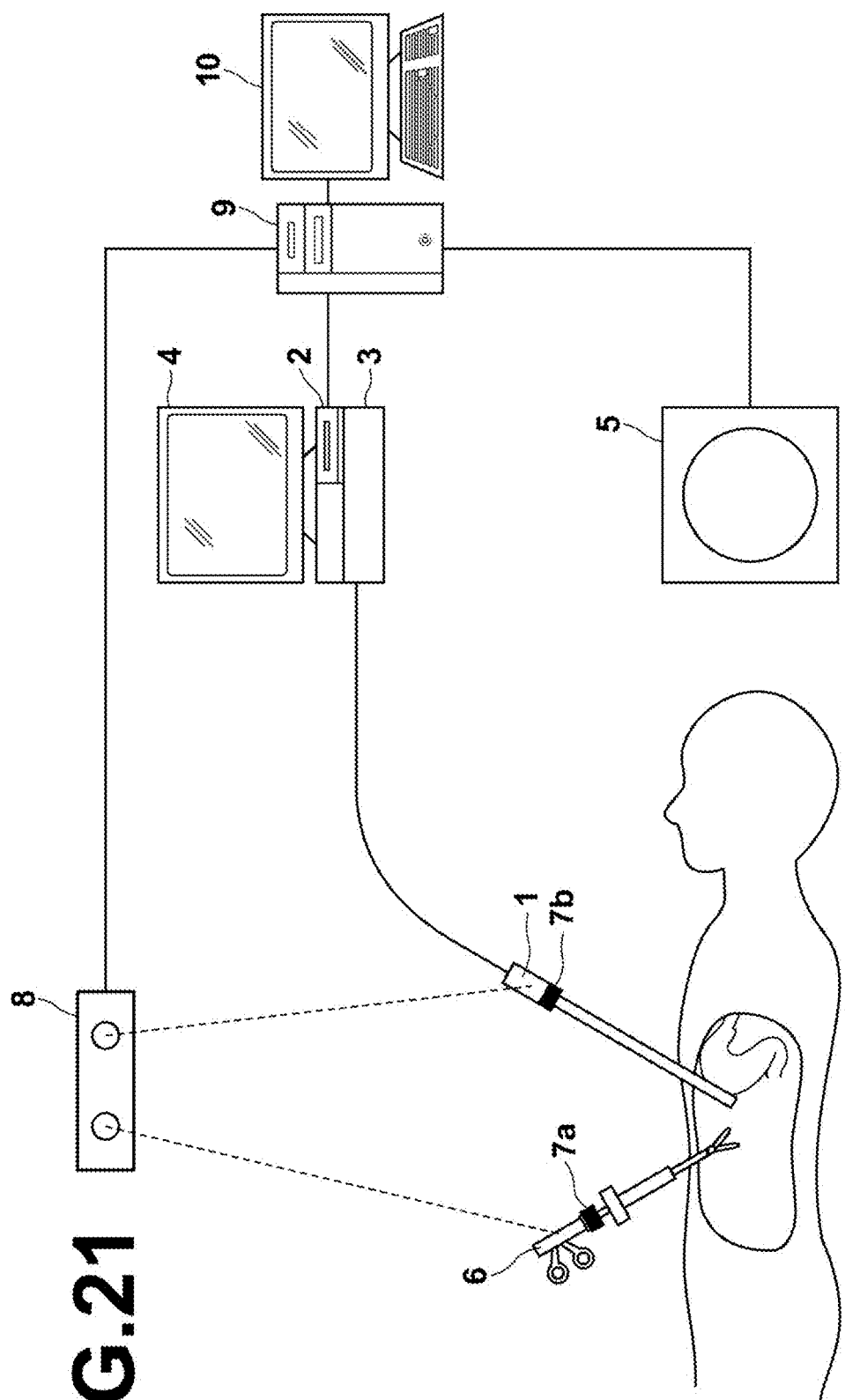
FIG. 21 is a diagram illustrating the hardware configuration of an endoscope observation assistance system according to a tenth embodiment of the present invention.
Figure 22:
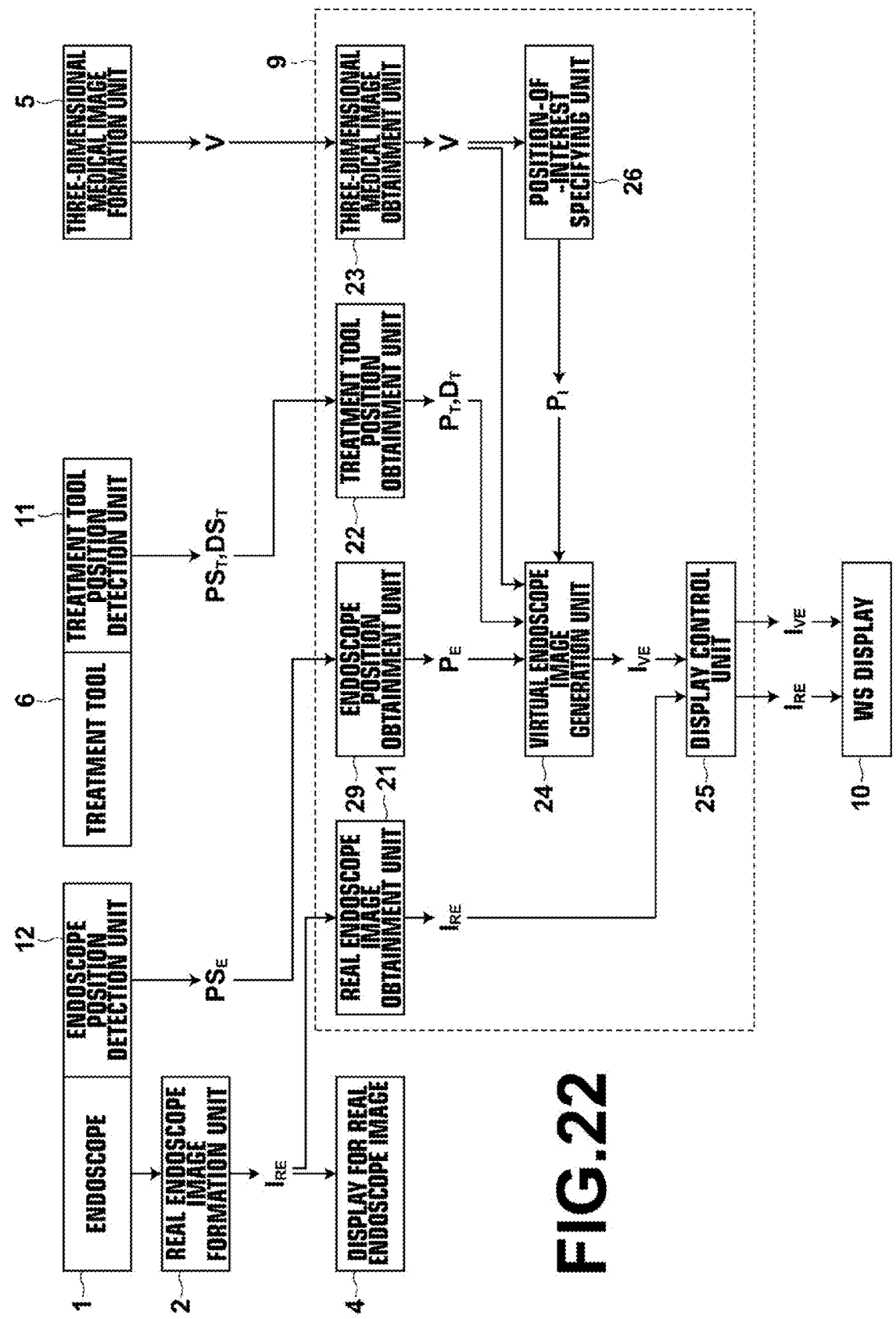
FIG. 22 is a functional block diagram illustrating the endoscope observation assistance system according to the tenth embodiment of the present invention.

FIG. 22 is a functional block diagram of the tenth embodiment of the present invention. An endoscope position detection unit 12 and an endoscope position obtainment unit 29 are added to the configuration of the third embodiment illustrated in FIG. 8. Here, the function of the endoscope position detection unit 12 is realized by the marker 7*b* for an endoscope and the position sensor 8 illustrated in FIG. 21. Further, endoscope position $P_E$ is data written in or read out from a predetermined memory area of the image processing workstation 8 by each processing unit in the broken line frame.

Figure 23:
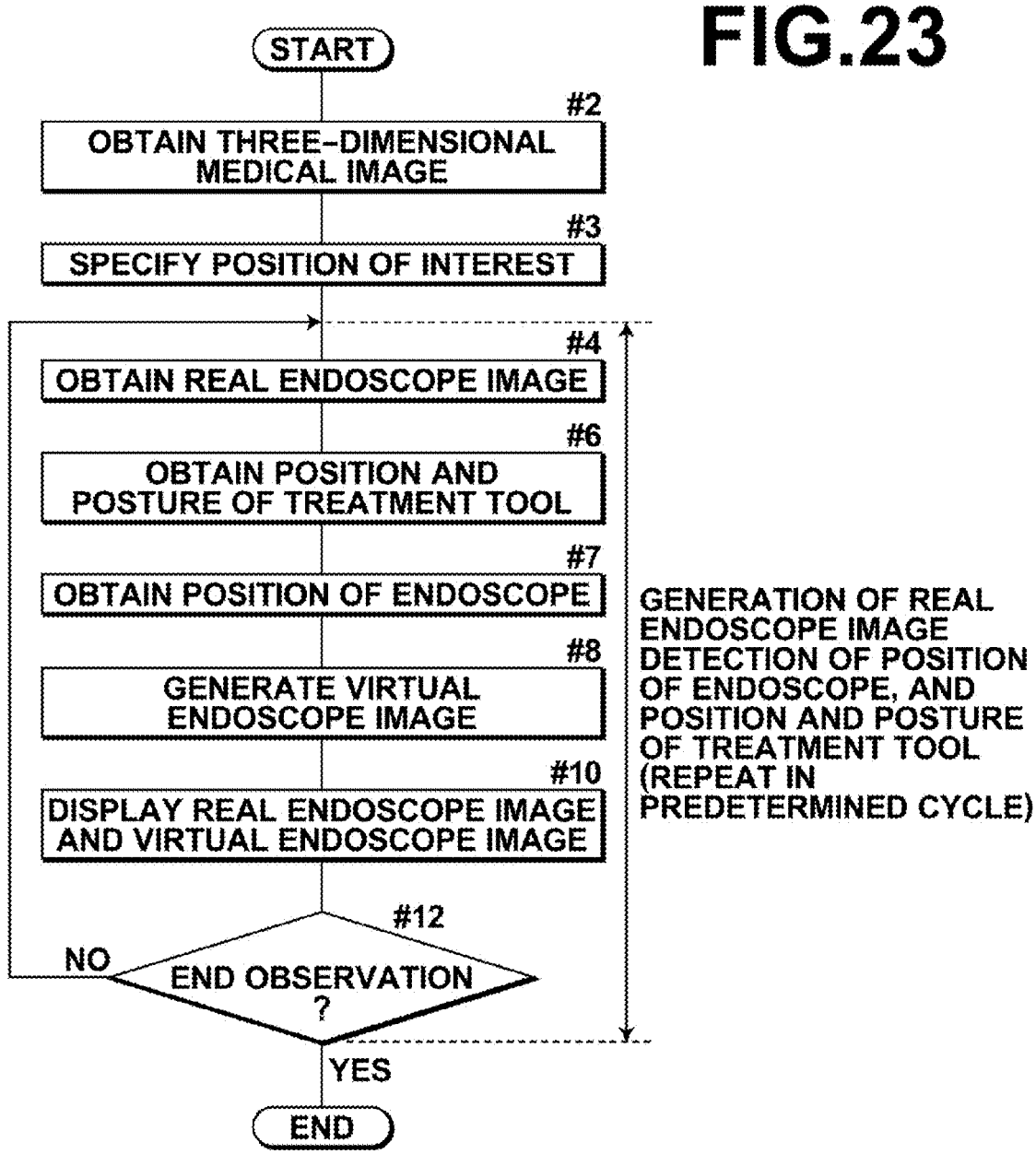
FIG. 23 is a flow chart illustrating a flow of endoscope observation assistance processing in the tenth embodiment of the present invention.

FIG. 23 is a flow chart illustrating a flow of endoscope observation assistance processing in the tenth embodiment of the present invention. As written on the right side of FIG. 23, during observation of the inside of the abnormal cavity of a subject to be examined by using an endoscope 1 until observation ends (#12; YES), the real endoscope image formation unit 2 repeats formation of real endoscope image $I_{RE}$. The treatment tool position detection unit 11 detects position $PS_T$ and posture $DS_T$ of the treatment tool 6, and the endoscope position detection unit 12 also repeats, in real time, detection of position $PS_E$ of the endoscope 1 inserted into the body cavity with predetermined time intervals. After the position and the posture of the treatment tool 6 have been obtained in step #6, the endoscope position obtainment unit 29 obtains the detected position $PS_E$ of the endoscope, which has been detected by the endoscope position detection unit 12. Further, the endoscope position obtainment unit 29 transforms the obtained position $PS_E$ of the endoscope into a position in the coordinate system of three-dimensional medical image V, and outputs the obtained endoscope position $P_E$ (#7).

When the virtual endoscope image generation unit 24 generates virtual endoscope image $I_{VE}$ the virtual endoscope image generation unit 24 generates, based on endoscope position $P_E$ obtained by the endoscope position obtainment unit 29, the virtual endoscope image $I_{VE}$ represented in such a manner that presence of the endoscope 1 at a position corresponding to endoscope position $P_E$ in the virtual endoscope image $I_{VE}$ is identifiable (#7). Processing (#10 through #12) after this is similar to the third embodiment.

Next, characteristics of each processing unit unique to this embodiment will be described in detail.

The endoscope position obtainment unit 29 has a function as a communication interface for obtaining endoscope detection position $PS_E$ by communication with the endoscope position detection unit 12 in a similar manner to the treatment tool position obtainment unit 22. The endoscope position obtainment unit 29 also has a function of transforming the obtained endoscope detection position $PS_E$ in the three-dimensional coordinate system of the position sensor 8 to endoscope position $P_E$ represented by a coordinate value in the three-dimensional coordinate system of the three-dimensional medical image V, and storing the endoscope position $P_E$ in a predetermined memory area of the image processing workstation 9.

Figure 24A:
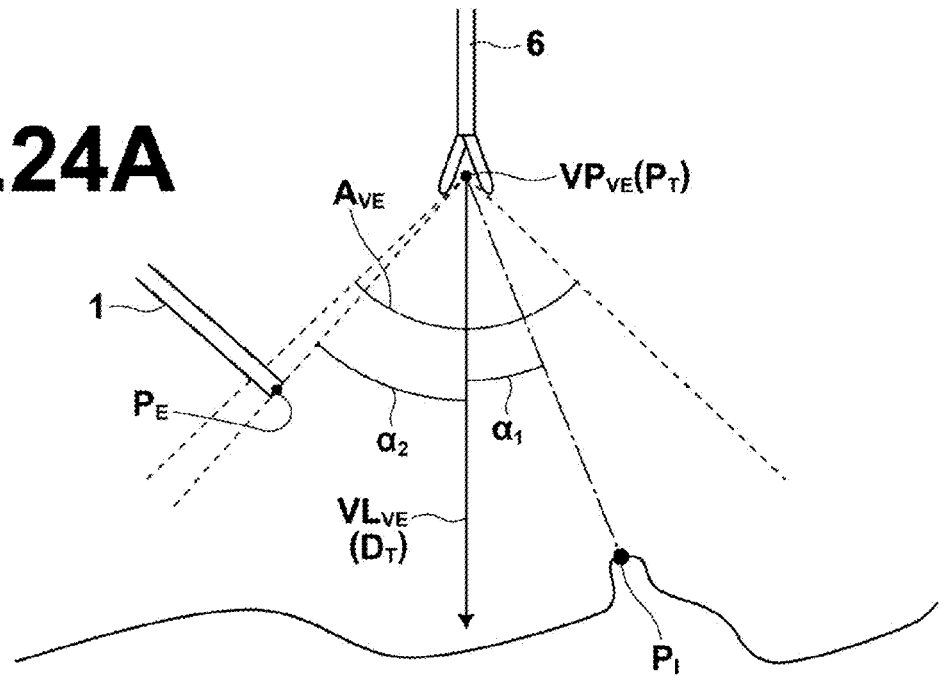
FIG. 24A is a schematic diagram illustrating an example of a positional relationship among a treatment tool, an endoscope and a structure of interest, and the position of a viewpoint, a center visual line and an angle of view of a virtual endoscope in the tenth embodiment of the present invention.

First, the virtual endoscope image generation unit 24 receives three-dimensional medical image V, as an input. As schematically illustrated in FIG. 24A, position $P_T$ of the treatment tool 6 is used as viewpoint position $VP_{VE}$ of a virtual endoscope, and posture vector $D_T$ of the treatment tool 6 is used as center visual line vector $VL_{VE}$ of the virtual endoscope. The virtual endoscope image generation unit 24 generates a virtual endoscope pre-image having angle $A_{VE}$ of view in such a manner that position $P_I$ of a structure of interest and position $P_E$ of the endoscope 1 are included in the field of view of the virtual endoscope. Here, when an angle formed between a vector connecting viewpoint position $VP_{VE}$ of the virtual endoscope and position $P_I$ of the structure of interest and center visual line vector $VL_{VE}$ of the virtual endoscope is $\alpha_1$, and angle formed between a vector connecting the viewpoint position $VP_{VE}$ of the virtual endoscope and endoscope position $P_E$ and center visual line vector $VL_{VE}$ of the virtual endoscope is $\alpha_2$, the virtual endoscope image generation unit 24 may obtain angle $A_{VE}$ of view of the virtual endoscope by adding a constant to the larger one of values $2\alpha_1$ and $2\alpha_2$, or by multiplying the larger one of values $2\alpha_1$ and $2\alpha_2$ by a predetermined coefficient that is larger than 1. In FIG. 24A, a distance between the endoscope position $P_E$ and the center of the field of view is longer than a distance between the position $P_I$ of the structure of interest and the center of the field of view. Therefore, the angle $A_{VE}$ of view is determined based on $2\alpha_2$.

Next, the virtual endoscope image generation unit 24 generates endoscope shape image $M_E$ representing a state in which the endoscope 1 is present at endoscope position $P_E$. Specifically, as described in Patent Document 2, the endoscope shape image $M_E$ is generated based on an image representing the shape of the endoscope 1 stored in a database and endoscope position $P_E$. The virtual endoscope image generation unit 24 generates virtual endoscope image $I_{VE}$ by combining the virtual endoscope pre-image and the endoscope shape image $M_E$ by using a known method, such as alpha blending. Instead of generating the endoscope shape image $M_E$ as described above, the virtual endoscope image $I_{VE}$ may be generated by superimposing a marker, such as an arrow and an icon, representing the endoscope 1 or an annotation, such as a text comment, at a position corresponding to endoscope position $P_E$ in the virtual endoscope pre-image.

Figure 24B:
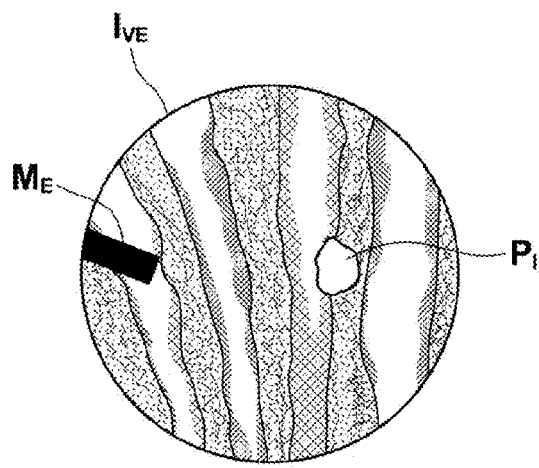
FIG. 24B is a schematic diagram illustrating an example of a virtual endoscope image in the tenth embodiment of the present invention.

FIG. 24B is a schematic diagram illustrating an example of virtual endoscope image $I_{VE}$ generated in the present embodiment. As illustrated in FIG. 24B, endoscope shape image $M_E$ is superimposed at a position corresponding to endoscope position $P_E$ in the virtual endoscope image $M_E$.

As described above, in the tenth embodiment of the present invention, virtual endoscope image $I_{VE}$ is generated in such a manner that not only position $P_I$ of the structure of interest but also position $P_E$ of the endoscope 1 is included in the field of view of the virtual endoscope image $I_{VE}$. Therefore, it is possible to definitely recognize a positional relationship and close proximity not only between the treatment tool 6 and the structure of interest but also among the treatment tool 6, the structure of interest and the endoscope 1.

At this time, virtual endoscope image $I_{VE}$ in which the field of view of the virtual endoscope and the content of an image are changed in real time based on feedback of a result of real-time detection of the position of the endoscope 1 by the endoscope position detection unit 12 is continuously displayed. Therefore, it is possible to dynamically and more accurately recognize the positional relationship and close proximity not only between the treatment tool 6 and the structure of interest but also among the treatment tool 6, the structure of interest and the endoscope 1.

Further, the real endoscope image formation unit 2 forms real endoscope image $I_{RE}$ representing the inside of the body cavity by imaging in real time by the endoscope 1, and real endoscope image $I_{RE}$ formed substantially at the same timing as detection of the positions of the endoscope 1 and the treatment tool 6 at the time of generation of the virtual endoscope image $I_{VE}$ is displayed. Therefore, the real endoscope image $I_{RE}$ and the virtual endoscope image $I_{VE}$ represent a state in the body cavity substantially at the same point in time. The real endoscope image $I_{RE}$ and the virtual endoscope image $I_{VE}$ are continuously displayed in such a manner that they are temporally synchronized with each other. At this time, the field of view of the real endoscope image $I_{RE}$ changes in such a manner to be linked with an operation, such as movement or rotation of the endoscope 1. Further, the field of view and the image content of the virtual endoscope image $I_{VE}$ change in such a manner to be linked with not only an operation of the treatment tool 6 but an operation of the endoscope 1. As described above, in the tenth embodiment of the present invention, it is possible to observe the inside of the body cavity in real time in such a manner that the real endoscope image $I_{RE}$ and the virtual endoscope image $I_{VE}$ supplement each other.

In an eleventh embodiment of the present invention, three-dimensional medical image V is formed and obtained in real time during endoscopic observation. In this case, the marker 7a for a treatment tool, the marker 7b for an endoscope, and the position sensor 8, which are provided in the hardware configuration of the tenth embodiment (please refer to FIG. 21), are not needed.

Figure 25:
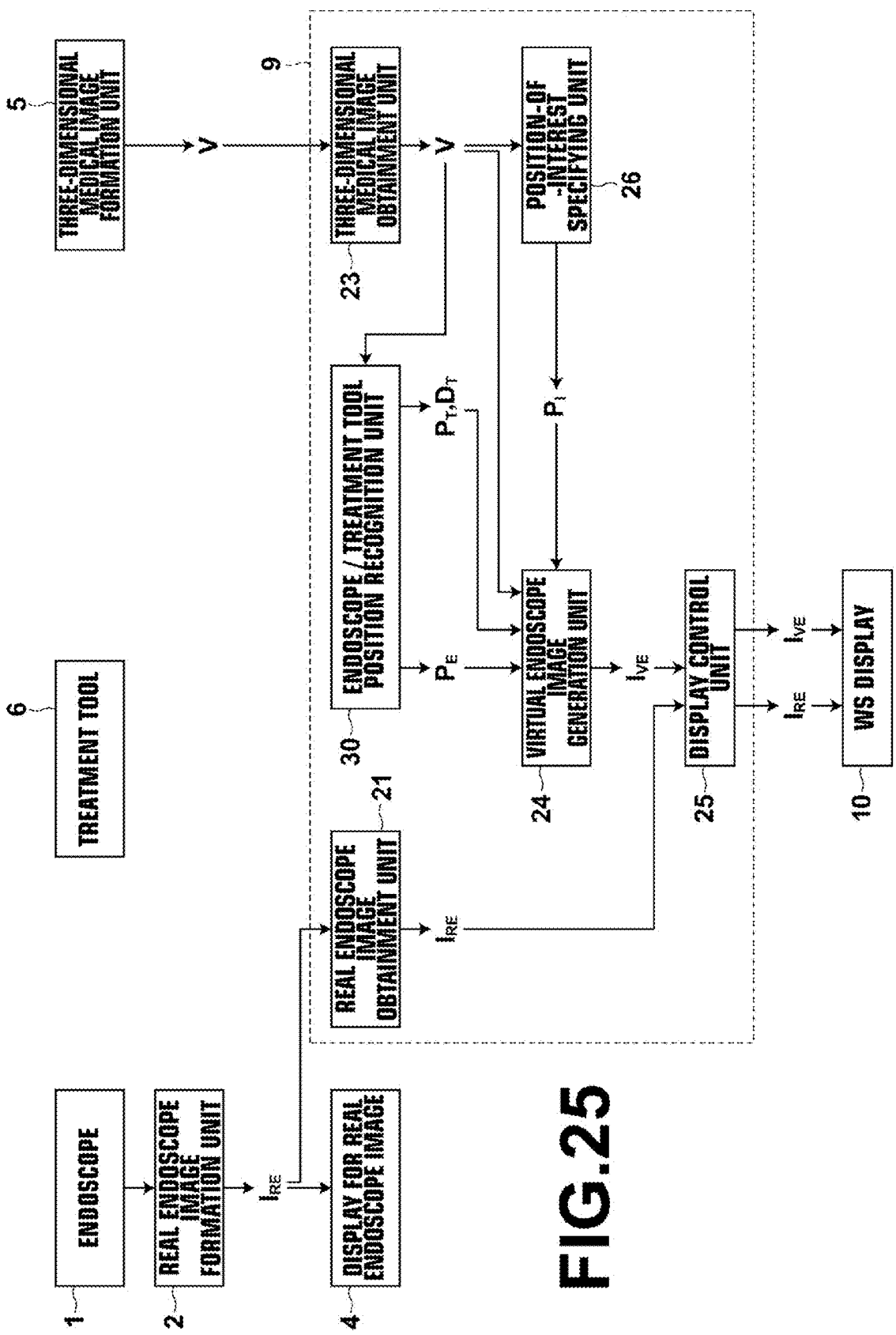
FIG. 25 is a functional block diagram illustrating an endoscope observation assistance system according to an eleventh embodiment of the present invention.

FIG. 25 is a functional block diagram of an endoscope observation assistance system in the eleventh embodiment of the present invention. As illustrated in FIG. 25, endoscope/treatment tool position recognition unit 30 is provided instead of the treatment tool position detection unit 11, the endoscope position detection unit 12, the treatment tool position obtainment unit 22 and the endoscope position obtainment unit 29 of the tenth embodiment. Specifically, the endoscope/treatment tool position recognition unit 30 corresponds to the position detection means of the present invention.

The endoscope/treatment tool position recognition unit 30 is a processing unit implemented in the image processing workstation 9. The endoscope/treatment tool position recognition unit 30 receives three-dimensional medical image V, as an input, and extracts a region representing an endoscope 1 or a treatment tool 6 in the three-dimensional medical image V by known pattern recognition processing. Further, the endoscope/treatment tool position recognition unit 30 recognizes endoscope position $P_E$, treatment tool position $P_T$ and treatment tool posture $D_T$.

FIG. 26 is a flow chart illustrating a flow of endoscope observation assistance processing in the eleventh embodiment of the present invention. As illustrated in FIG. 26, after real endoscope image $I_{RE}$ is obtained in step #4, the three-dimensional medical image obtainment unit 24 obtains three-dimensional medical image V (#6.1). The endoscope/treatment tool position recognition unit 30 recognizes endoscope position $P_E$, treatment tool position $P_T$ and treatment tool posture $D_T$ based on three-dimensional medical image V obtained by the three-dimensional medical image obtainment unit 24 (#6.2). In step #8, the virtual endoscope image generation unit 24 generates virtual endoscope image $I_{VE}$ by using a color template defined in such a manner that a region representing the endoscope 1 extracted by the endoscope/treatment tool position recognition unit 30 is displayed in a predetermined color. Therefore, it is not necessary to generate a shape image of the endoscope 1 as in the tenth embodiment. As described above, if the three-dimensional medical image V is formed and obtained in real time during endoscopic observation, the obtained three-dimensional medical image V represents the state of the inside of the abdominal cavity substantially at the same time as the real endoscope image $I_{RE}$. Therefore, virtual endoscope image $I_{VE}$ in which the real condition of the inside of the abdominal cavity is more accurately regenerated in real time than the case of using three-dimensional medical image V obtained before endoscopic observation is generated. However, in this embodiment, when the three-dimensional medical image V is imaged in step #2 and step #6.1, it is necessary to pay attention to the posture of a patient's body so that the position of the subject to be examined corresponding to the origin of coordinate axes and the directions of the coordinate axes do not change.

In the eleventh embodiment, it is desirable that an ultrasonic diagnosis apparatus is used as a modality 5 to reduce the dose of radiation irradiating the subject to be examined.

The aforementioned embodiments are described only as examples. Therefore, none of the descriptions should be used to narrowly interpret the technical range of the present invention.

Further, the system configuration, the hardware configuration, the process flow, the module configuration, the user interface, specific processing content, and the like may be modified in various manners without deviating from the gist of the present invention. Such modifications are still in the technical scope of the present invention.

For example, with respect to the system configuration, in the aforementioned embodiments, the modality 5 and the image processing workstation 9 are directly connected to each other in the hardware configuration illustrated in FIGS. 1 and 21. Alternatively, an image storage server may be connected to LAN, and three-dimensional medical image V formed in the modality 5 may be temporarily stored in a database in the image storage server. Further, the three-dimensional medical image V may be transferred from the image storage server to the image processing workstation 9 based on a request from the image processing workstation 9.

Further, it is not necessary that the endoscope 1 is a rigid endoscope. Alternatively, a fiber scope or a capsule-type endoscope may be used.

As the modality 5, an MRI apparatus or the like may be used besides the CT apparatus and the ultrasonic diagnosis apparatus as described above.

The WS display 10 may be a display that can cope with known stereoscopic display. The WS display 10 may display virtual endoscope image $I_{VE}$ as an image for stereoscopic display. For example, when the WS display 10 adopts a method for realizing stereoscopic display by using two parallax images for the left and right eyes, the virtual endoscope image generation unit 24 should set the position of each eye shifted by the amounts of parallax of the left and right eyes from viewpoint position $VP_{VE}$, respectively. Further, the virtual endoscope image generation unit 24 should perform center projection using the set position of each eye as a viewpoint, and generate a virtual endoscope parallax image for each of the left and right eyes. Further, the display control unit 25 should control in such a manner that the virtual endoscope parallax image for the left eye is displayed by using display pixels for the left eye in the WS display 10, and that the virtual endoscope parallax image for the right eye is displayed by using display pixels for the right eye in the WS display 10.

The treatment tool position detection unit 11 and the endoscope position detection unit 12 may be magnetic type units. Alternatively, a gyro, a rotary encoder and the like may be used as described in Patent Document 2.

Further, it is not necessary that the observation region is the inside of the abdominal cavity. The observation region may be a different region of the subject to be examined, such as the thoracic cavity, which is appropriate for endoscopic observation.

In the image processing workstation 9, the cycle of forming real endoscope images $I_{RE}$ by the real endoscope image formation unit 2 is shorter than the cycle of generating virtual endoscope images $I_{VE}$ by the virtual endoscope image generation unit 24 in the aforementioned embodiments. Further, a load of communication is considered, and an image is received based on a request from the real endoscope image obtainment unit 21. Alternatively, all of real endoscope images $I_E$ sequentially formed by the real endoscope image formation unit 2 may be received by the real endoscope image obtainment unit 21. In this case, the display control unit 25 may update the display of the real endoscope image $I_{EE}$ on the WS display 10 every time when the real endoscope image $I_{RE}$ is received in such a manner to be non-synchronized with the timing of generating the virtual endoscope image $I_{VE}$ by the virtual endoscope image generation unit 24.

The treatment tool position obtainment unit 22 may receive all of positions $PS_T$ and postures $DS_T$ of the treatment tool detected by the treatment tool position detection unit 11 with predetermined time intervals. Further, the treatment tool position obtainment unit 22 may transform only position $PS_T$ and posture $DS_T$ of the treatment tool that have been received at timing of calling processing of step #4 illustrated in FIG. 3 or the like into treatment tool position $P_E$ and posture $D_T$ by the coordinate transformation function, and output the treatment tool position $P_E$ and posture $D_T$. Further, the endoscope position obtainment unit 29 may perform processing in a similar manner.

The coordinate transformation performed by the treatment tool position obtainment unit 22 and the endoscope position obtainment unit 29 may be performed by the virtual endoscope image generation unit 24.

The position-of-interest specifying unit 26 may automatically specify a position of interest by using a known image recognition technique (a method for extracting a blood vessel or an organ, an abnormal shadow detection method, or the like).

Further, the virtual endoscope image generation unit 24 may further generate a virtual endoscope image using, as viewpoints, plural positions of interest, for example, such as a region on which a surgery is to be performed, a caution-required blood vessel, a caution-required organ, and a treatment tool.

The invention claimed is:

1. An endoscope observation assistance system comprising:
    an image formation system configured to form a three-dimensional medical image representing a body cavity of a subject to be examined;
    a treatment tool position detection system that detects, in real time, a position of a treatment tool inserted into the body cavity and detects a direction in which the treatment tool moves straight forward at the same time as detection of the position of the treatment tool;
    one or more image processors configured to generate a virtual endoscope image, the one or more image processors receiving the three-dimensional medical image as an input, and generating a virtual endoscope image representing the body cavity viewed from a corresponding treatment tool position, which is a position in the three-dimensional medical image corresponding to the detected position of the treatment tool; and
    a display that displays the virtual endoscope image,
    wherein the one or more image processors generate the virtual endoscope image in which image information on a treatment tool visual line from the corresponding treatment tool position is projected, the treatment tool visual line having a direction in the three-dimensional medical image corresponding to the direction in which the treatment tool moves straight forward,
    the one or more image processors generate the virtual endoscope image that identifiably represents a position in the virtual endoscope image at which the image information on the treatment tool visual line has been projected, and an insertion position of the body surface at which the treatment tool is inserted into the body cavity differs from an insertion position of the body surface at which an endoscope is inserted into the body cavity.

2. The endoscope observation assistance system, according to claim 1, wherein the one or more image processors generate the virtual endoscope image by determining an angle of view of the virtual endoscope image in such a manner that the specified position of interest is included in a field of view of the virtual endoscope image.

3. The endoscope observation assistance system, according to claim 1, wherein one or more image processors generate the virtual endoscope image in which the treatment tool visual line is a center visual line, which is a visual line at the center of the field of view of the virtual endoscope image.

4. The endoscope observation assistance system, according to claim 1, wherein the one or more image processors specify, as a position of interest, a position of a structure of interest in the body cavity in the three-dimensional medical image, and
the one or more image processors generate the virtual endoscope image in which a visual line from the corresponding treatment tool position toward the specified position of interest is a center visual line of the virtual endoscope image.

5. The endoscope observation assistance system, according to claim 1, wherein the one or more image processors generate the virtual endoscope image that identifiably represents at least a position of interest in a structure of interest.

6. The endoscope observation assistance system, according to claim 5, wherein the one or more image processors detect, in the three-dimensional medical image, a second structure of interest in the body cavity, and
wherein the one or more image processors generate the virtual endoscope image that identifiably represents the second structure of interest.

7. The endoscope observation assistance system, according to claim 6, wherein one of the structure of interest and the second structure of interest is a region on which an endoscopic surgery is to be performed, and the other one of the structure of interest and the second structure of interest is an anatomical structure that requires caution in the endoscopic surgery.

8. The endoscope observation assistance system, according to claim 1,
wherein the one or more image processors present a warning when the corresponding treatment tool position and a structure of interest are close to each other to such an extent to satisfy a predetermined criterion.

9. The endoscope observation assistance system, according to claim 1, wherein a structure of interest is a region on which an endoscopic surgery is to be performed.

10. The endoscope observation assistance system, according to claim 1, wherein a structure of interest is an anatomical structure that requires caution in an endoscopic surgery.

11. The endoscope observation assistance system, according to claim 1, wherein the one or more image processors determine pixel values of the virtual endoscope image based on a distance from the corresponding treatment tool position to a surface of a structure in the body cavity.

12. The endoscope observation assistance system, according to claim 1, wherein the one or more image processors determine pixel values of the virtual endoscope image by using a color template that is defined so that an external view of each part in the body cavity represented in the virtual endoscope image is substantially the same as an external view of each part in the body cavity represented in a real endoscope image obtained by imaging by an endoscope.

13. The endoscope observation assistance system, according to claim 1, the system further comprising:
a real endoscope image formation processor that forms a real endoscope image representing the body cavity by imaging in real time by an endoscope,
wherein the display further displays the real endoscope image formed substantially at the same timing as detection of the position of the treatment tool used at the time of generation of the virtual endoscope image.

14. The endoscope observation assistance system as defined in claim 1, wherein the one or more image processors specify, as a position of interest, a position of a structure of interest in the body cavity in the three-dimensional medical image, and
the one or more image processors generate a virtual endoscope image, a field of view of which includes the specified position of interest.

15. An endoscope observation assistance system, comprising:
an image formation system configured to form a three-dimensional medical image representing a body cavity of a subject to be examined;
a treatment tool position detection system that detects, in real time, a position of a treatment tool inserted into the body cavity;
one or more image processors configured to generate a virtual endoscope image, the one or more image processors receiving the three-dimensional medical image as an input, and generating the virtual endoscope image representing the body cavity viewed from a corresponding treatment tool position, which is the same position in the three-dimensional medical image as the detected position of the treatment tool;
a display that displays the virtual endoscope image; and
an endoscope position detection system that detects the position of an endoscope inserted into the body cavity,
wherein the one or more image processors generate the virtual endoscope image, a field of view of which includes a corresponding endoscope position, which is the same position in the three-dimensional medical image as the detected position of the endoscope, the virtual endoscope image identifiably representing the corresponding endoscope position,
an insertion position of the body surface at which the treatment tool is inserted into the body cavity differs from an insertion position of the body surface at which the endoscope is inserted into the body cavity, and
the one or more image processors generate the virtual endoscope image in which image information on a treatment tool visual line from the corresponding treatment tool position is projected.

16. An endoscope observation assistance method comprising:
forming a three-dimensional medical image representing a body cavity of a subject to be examined;
detecting, in real time, a position of a treatment tool inserted into the body cavity;
detecting a direction in which the treatment tool moves straight forward at the same time as detection of the position of the treatment tool;
receiving the three-dimensional medical image as an input, and generating a virtual endoscope image representing the body cavity viewed from a corresponding treatment tool position, which is a position in the three-dimensional medical image corresponding to the detected position of the treatment tool; and displaying the virtual endoscope image, wherein the virtual endoscope image is generated in which image information on a treatment tool visual line from the corresponding treatment tool position is projected, the treatment tool visual line having a direction in the three-dimensional medical image corresponding to the direction in which the treatment tool moves straight forward, the virtual endoscope image that is generated identifiably represents a position in the virtual endoscope image at which the image information on the treatment tool visual line has been projected, and an insertion position of the body surface at which the treatment tool is inserted into the body cavity differs from an insertion position of the body surface at which the endoscope is inserted into the body cavity.

17. An endoscope observation assistance apparatus comprising:

one or more image processors configured to obtain a three-dimensional medical image representing a body cavity of a subject to be examined, obtain a position of a treatment tool inserted into the body cavity and a direction in which the treatment tool moves straight forward, the position having been detected in real time by a treatment tool position detection system, the direction in which the treatment tool moves straight forward having been detected by the treatment tool position detection system at the same time as detection of the position of the treatment tool, and receive the three-dimensional medical image as an input, and generate a virtual endoscope image representing the body cavity viewed from a corresponding treatment tool position, which is a position in the three-dimensional medical image corresponding to the obtained position of the treatment tool; and a display controller that makes a display display the virtual endoscope image, wherein the one or more image processors generate the virtual endoscope image in which image information on a treatment tool visual line from the corresponding treatment tool position is projected, the treatment tool visual line having a direction in the three-dimensional medical image corresponding to the direction in which the treatment tool moves straight forward, the one or more image processors generate the virtual endoscope image that identifiably represents a position in the virtual endoscope image at which the image information on the treatment tool visual line has been projected, and an insertion position of the body surface at which the treatment tool is inserted into the body cavity differs from an insertion position of the body surface at which the endoscope is inserted into the body cavity.

18. A non-transitory computer-readable storage medium storing therein an endoscope observation assistance program for causing a computer to execute the steps of:

obtaining a three-dimensional medical image representing a body cavity of a subject to be examined;

obtaining a position of a treatment tool inserted into the body cavity, the position having been detected in real time by a treatment tool position detection system;

obtaining a direction in which the treatment tool moves straight forward, the direction in which the treatment tool moves straight forward having been detected at the same time as detection of the position of the treatment tool;

receiving the three-dimensional medical image as an input, and generating a virtual endoscope image representing the body cavity viewed from a corresponding treatment tool position, which is a position in the three-dimensional medical image corresponding to the obtained position of the treatment tool; and making a display display the virtual endoscope image, wherein the virtual endoscope image is generated in which image information on a treatment tool visual line from the corresponding treatment tool position is projected, the treatment tool visual line having a direction in the three-dimensional medical image corresponding to the direction in which the treatment tool moves straight forward, the virtual endoscope image that is generated identifiably represents a position in the virtual endoscope image at which the image information on the treatment tool visual line has been projected, and an insertion position of the body surface at which the treatment tool is inserted into the body cavity differs from an insertion position of the body surface at which the endoscope is inserted into the body cavity.

19. An endoscope observation assistance method comprising:

forming a three-dimensional medical image representing a body cavity of a subject to be examined;

detecting, in real time, a position of a treatment tool inserted into the body cavity;

detecting a position of an endoscope inserted into the body cavity;

receiving the three-dimensional medical image as an input, and generating a virtual endoscope image representing the body cavity viewed from a corresponding treatment tool position, which is the same position in the three-dimensional medical image as the detected position of the treatment tool; and displaying the virtual endoscope image, wherein a field of view of the generated virtual endoscope image includes a corresponding endoscope position, which is the same position in the three-dimensional medical image as the detected position of the endoscope, the virtual endoscope image identifiably representing the corresponding endoscope position, an insertion position of the body surface at which the treatment tool is inserted into the body cavity differs from an insertion position of the body surface at which the endoscope is inserted into the body cavity, and the virtual endoscope image is generated in which image information on a treatment tool visual line from the corresponding treatment tool position is projected.

20. An endoscope observation assistance apparatus comprising:

one or more image processors configured to obtain a three-dimensional medical image representing a body cavity of a subject to be examined, obtain a position of a treatment tool inserted into the body cavity, the position having been detected in real time by a treatment tool position detection system, obtain a position of an endoscope inserted into the body cavity, and receive the three-dimensional medical image as an input, and generate a virtual endoscope image representing the body cavity viewed from a corresponding treatment tool position, which is the same position in the three-dimensional medical image as the obtained position of the treatment tool; and a display controller that makes a display display the virtual endoscope image, wherein a field of view of the generated virtual endoscope image includes a corresponding endoscope position, which is the same position in the three-dimensional medical image as the detected position of the endoscope, the virtual endoscope image identifiably representing the corresponding endoscope position, an insertion position of the body surface at which the treatment tool is inserted into the body cavity differs from an insertion position of the body surface at which the endoscope is inserted into the body cavity, and the one or more image processors generate the virtual endoscope image in which image information on a treatment tool visual line from the corresponding treatment tool position is projected.

21. A non-transitory computer-readable storage medium storing therein an endoscope observation assistance program for causing a computer to execute the steps of:

obtaining a three-dimensional medical image representing a body cavity of a subject to be examined;

obtaining a position of a treatment tool inserted into the body cavity, the position having been detected in real time by a treatment tool position detection system;

obtain a position of an endoscope inserted into the body cavity, receiving the three-dimensional medical image as an input, and generating a virtual endoscope image representing the body cavity viewed from a corresponding treatment tool position, which is the same position in the three-dimensional medical image as the obtained position of the treatment tool; and making a display display the virtual endoscope image, wherein a field of view of the generated virtual endoscope image includes a corresponding endoscope position, which is the same position in the three-dimensional medical image as the detected position of the endoscope, the virtual endoscope image identifiably representing the corresponding endoscope position, an insertion position of the body surface at which the treatment tool is inserted into the body cavity differs from an insertion position of the body surface at which the endoscope is inserted into the body cavity, and the virtual endoscope image is generated in which image information on a treatment tool visual line from the corresponding treatment tool position is projected.

* * * * *